(12) United States Patent
Farren

(10) Patent No.: US 9,044,521 B2
(45) Date of Patent: Jun. 2, 2015

(54) UV STERILIZATION OF CONTAINERS

(76) Inventor: Alexander Farren, Hayward, CA (US)

( * ) Notice: Subject to any disclaimer, the term of this patent is extended or adjusted under 35 U.S.C. 154(b) by 242 days.

(21) Appl. No.: 13/151,196

(22) Filed: Jun. 1, 2011

(65) Prior Publication Data

US 2011/0305597 A1  Dec. 15, 2011

Related U.S. Application Data

(60) Provisional application No. 61/350,414, filed on Jun. 1, 2010.

(51) Int. Cl.
*A61L 2/00* (2006.01)
*H01J 37/20* (2006.01)
*A61L 2/10* (2006.01)

(52) U.S. Cl.
CPC ........................................ *A61L 2/10* (2013.01)

(58) Field of Classification Search
USPC ........................................ 422/24; 250/455.11
See application file for complete search history.

(56) References Cited

U.S. PATENT DOCUMENTS

| | | | |
|---|---|---|---|
| 1,788,906 A * | 1/1931 | Brown ...................... 250/453.11 |
| 2,194,463 A | 3/1940 | Powley |
| 3,906,236 A | 9/1975 | Callahan |
| 4,396,582 A * | 8/1983 | Kodera .......................... 422/300 |
| 4,786,812 A | 11/1988 | Humphreys |
| 4,830,968 A | 5/1989 | Thornton et al. |
| 4,871,559 A * | 10/1989 | Dunn et al. .................... 426/248 |
| 5,020,183 A | 6/1991 | Grant, Jr. |
| 5,597,597 A | 1/1997 | Newman |
| 5,744,094 A * | 4/1998 | Castberg et al. ................. 422/24 |
| 5,920,075 A | 7/1999 | Whitehead |
| 6,074,565 A * | 6/2000 | Buckner ........................ 210/764 |
| 6,299,770 B1 | 10/2001 | Diener |
| 6,368,554 B1 * | 4/2002 | Wajsfelner et al. ............. 422/22 |
| 6,403,030 B1 | 6/2002 | Horton, III |
| 6,517,776 B1 * | 2/2003 | Rodgers et al. ................. 422/24 |
| 6,953,940 B2 | 10/2005 | Leighley |

(Continued)

FOREIGN PATENT DOCUMENTS

| | | |
|---|---|---|
| DE | 4407183 A1 | 7/1995 |
| DE | 29812427 U1 | 1/1999 |

(Continued)

OTHER PUBLICATIONS

International Search Report and Written Opinion under Patent Cooperation Treat (PCT) for PCT/US2011/38826; Sep. 12, 2011; 8 pages.

(Continued)

*Primary Examiner* — Kevin Joyner
(74) *Attorney, Agent, or Firm* — Duane Morris LLP; Siegfried Ruppert

(57) ABSTRACT

Provided herein are systems, devices, and methods for ultraviolet (UV) disinfection and sterilization, more specifically, systems, devices, and methods for UV disinfection and sterilization of a container, and more particularly systems, devices, and methods for UV disinfection and sterilization of a container used in the process of fermentation for an alcoholic beverage. Provided are also systems, UV devices, and methods for inhibiting the growth of one or more species of microorganisms present in a container, preferably for inhibiting the growth of one or more species of microorganisms present on an interior surface of a container.

107 Claims, 20 Drawing Sheets

(56) References Cited

U.S. PATENT DOCUMENTS

| | | |
|---|---|---|
| 7,081,636 B2 * | 7/2006 | Moruzzi .................. 250/504 R |
| 7,829,016 B2 * | 11/2010 | Deal et al. .................. 422/24 |
| 2002/0063954 A1 | 5/2002 | Horton |
| 2002/0122743 A1 | 9/2002 | Huang |
| 2003/0067768 A1 | 4/2003 | Shiau |
| 2006/0011263 A1 * | 1/2006 | Till .................. 141/147 |
| 2006/0032199 A1 | 2/2006 | Beam |
| 2006/0284109 A1 | 12/2006 | Scheir |
| 2007/0140435 A1 | 6/2007 | Schwieker |
| 2008/0199353 A1 | 8/2008 | Mlodzinski |
| 2008/0206095 A1 | 8/2008 | Duthie |
| 2008/0240978 A1 | 10/2008 | Sorensen et al. |
| 2009/0010826 A1 | 1/2009 | Shin |
| 2009/0274576 A1 | 11/2009 | Ressler |
| 2010/0266445 A1 | 10/2010 | Campagna |
| 2011/0079590 A1 | 4/2011 | Lin |
| 2011/0143000 A1 | 6/2011 | Fiset |
| 2011/0286883 A1 | 11/2011 | Hecht |
| 2012/0121457 A1 | 5/2012 | Farren |

FOREIGN PATENT DOCUMENTS

| | | |
|---|---|---|
| EP | 1120121 A2 | 1/2001 |
| GB | 495499 A | 11/1938 |
| GB | 556912 A | 10/1943 |
| GB | 2454642 A | 5/2009 |
| WO | WO90/05909 | 5/1990 |
| WO | WO 02/36437 A1 | 5/2002 |
| WO | WO2007/035907 | 3/2007 |
| WO | WO 2009/086053 A1 | 7/2009 |
| WO | WO2010/021506 A2 | 2/2010 |
| WO | WO2010/133698 A2 | 11/2010 |
| WO | WO 2011/153288 A1 | 12/2011 |

OTHER PUBLICATIONS

International Search Report and Written Opinion under Patent Cooperation Treat (PCT) for PCT/US11/63827; Dated Apr. 18, 2012; 10 pages.

* cited by examiner

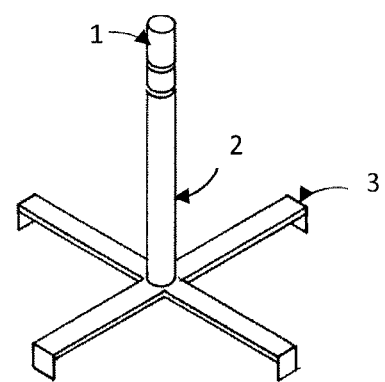
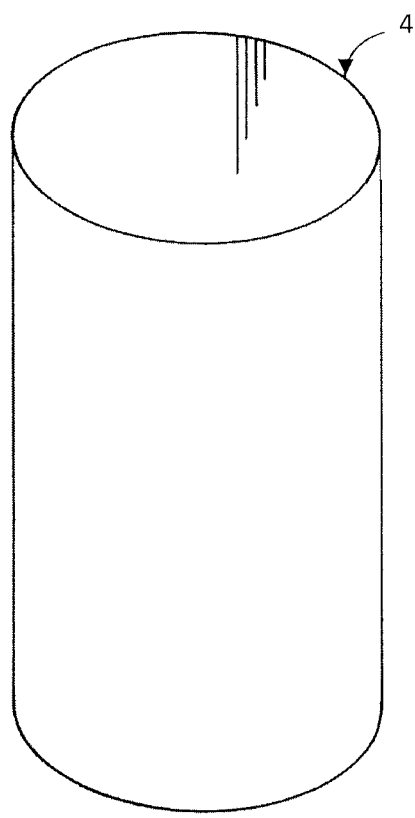
Figure 1

| Length | Model | Description | Type* | Diameter/Base | UVC Output Watts | UV pW/cm² @1m |
|---|---|---|---|---|---|---|
| 6" | GML370 | Hot Cathode | PL-S9W/TUV | PL-S | 2.4 | |
| | GML180 | Hot Cathode | G 4T5 | T5/mini bi-pin | 0.5 | 5.4 |
| | GML170 | Hot Cathode | OZ4T5 | T5/mini bi-pin | 0.5 | 5.4 |
| 9" | GML195 | Hot Cathode | G 6T5 | T5/mini bi-pin | 1.0 | 11 |
| | GML190 | Hot Cathode | OZ 6T5 | T5/mini bi-pin | 1.1 | 11 |
| 12" | GML205 | Hot Cathode | G 8T5 | T5/mini bi-pin | 1.6 | 17 |
| | GML125 | Slimline | G12T5½L/BP | T5/mini bi-pin | 6.0 | 66 |
| | GML075 | Slimline | G12T5½VH/BP | T5/mini bi-pin | 6.0 | 66 |
| | GML405 | High Output | GPH357T5L/HO | Four-pin | 8.5 | 92 |
| 14" | AAWHO/14 | High Output | Custom | Four-pin | 12 | 106 |
| 16" | GML020 | Cold Cathode | 782 L 10 | T5/single-pin | 2.0/2.8 | 20/28 |
| | GML120 | Cold Cathode | 782 VH 10 | T5/single-pin | 2.0/2.8 | 20/28 |
| | GML060 | Slimline | G10T5½L | T5/single-pin | 5.3 | 55 |
| | GML350 | Slimline | G10T5½L-4P | T5/four-pin | 5.3 | 55 |
| | GML070 | Slimline | G10T5½LVH | T5/single-pin | 5.3 | 55 |
| 18" | GML430 | Hot Output | GSL406T5L/HO | Four-pin | 10.0 | 108 |
| | GML210 | Hot Cathode | G15T8 | T8/medium bi-pin | 3.6 | 38 |
| | GML215 | Hot Cathode | G25T8 | T8/medium bi-pin | 5.0 | 54 |
| | GML410 | High Output | GSL406T5L/HO | Single-pin | 10.0 | 100 |
| 22" | AAWHO/22 | High Output | GPH550T5/HO/4 | Four-pin | 18 | 174 |
| | GML225MBP | High Output | CUSTOM | T5 15mm Bi-pin | 18 | 157 |
| 24" | GML435 | High Output | GPH610T5L/HO | Four-pin | 16.2 | 175 |
| | GML0224/4PNO | High Output | CUSTOM | T5 15mm Four-pin | 20 | 168 |
| | GML0244PO | High Output | CUSTOM | T5 15mm Four-pin | 20 | 168 |
| 27" | GML025 | Cold Cathode | 782 L 20 | T5/single-pin | 3.9/5.5 | 35/52 |
| | GML290 | Cold Cathode | 782 VH 20 | T5/single-pin | 3.9/5.5 | 35/52 |
| | GML325 | Slimline | GSL591 | T5/single-pin | | |
| | GML355 | Slimline | S24T5-4P | T5/four-pin | | |
| | GML415 | High Output | GPH610T5L/HO | Single-pin | 16.2 | 140 |
| 30" | GML030 | Cold Cathode | 782 L 25½ | T5/single-pin | 7.3 | 75 |
| 36" | GML010 | Cold Cathode | 782 L 30 | T5/single-pin | 5.2/8.3 | 46/73 |
| | GML035 | Cold Cathode | 782 VH 29 | T5/mini bi-pin | 5.7/9.1 | 50/80 |
| | GML040 | Cold Cathode | 782 H 30 | T5/single-pin | 5.2/8.3 | 46/73 |
| | GML220 | Hot Cathode | G30T8 | T8/medium bi-pin | 8.3 | 85 |
| | GML005 | Slimline | G36T6L | T5/single-pin | 13.8 | 120 |
| | GML100 | Slimline | G36T6L-4P | T5/four-pin | 12.7 | 110 |
| | GML090 | Slimline | G36T6VH | T5/single-pin | 13.8 | 120 |
| | GML095 | Slimline | G37T6VH | T5/single-pin | 15.2 | 124 |
| | GML420 | High Output | GSL843T5L/HO | Single-pin | 25 | 195 |
| | GML440 | High Output | GSL843T5L/HO/4 | Four-pin | 25 | 195 |
| 48" | GML425 | High Output | GSL1148T5L/HO | Single-pin | 36.1 | 250 |
| | GML445 | High Output | GSL1148T5L/HO/4 | Four-pin | 36.1 | 250 |
| 64" | GML015 | Slimline | G64T5L | T5/single-pin | 26.7 | 190 |
| | GML017 | High Output | GXO64T5L H/O | Single-pin | 46 | 370 |
| | GML140 | Slimline | G84T5VH | T5/single-pin | 26.7 | 190 |
| | GML270 | Slimline | G64T5L-4P | T5/four-pin | 26.7 | 190 |

*FIG. 17*

3.5" Elliptical
12' Sections 1.75" Elliptical
10' Sections

5" Parabolic Diffuser
10' Sections

7" Parabolic Diffuser
10' Sections

UV STERILIZATION OF CONTAINERS

CROSS-REFERENCE TO RELATED APPLICATIONS

This patent application claims the benefit of U.S. provisional patent application Ser. No. 61/350,414, entitled "UV Sterilization Of Containers" and filed Jun. 1, 2010, the disclosure of which is incorporated herein by reference in its entirety by reference for all purposes.

FIELD OF INVENTION

The present invention relates generally to systems and methods for ultraviolet (UV) disinfection, and more specifically, to systems and methods for UV disinfection of a container, and more particularly to systems and methods for UV disinfection of a container used in the process of fermentation for an alcoholic beverage.

BACKGROUND OF THE INVENTION

It has been well established that ultraviolet (UV) light has germicidal properties. Specifically, the mechanism by which UV light kills microorganisms is by damaging the genetic material, the deoxyribonucleic acid (DNA), of the microorganisms. Wavelengths between 200-300 nm have been shown to initiate a photoreaction between adjacent pyrimidines. Pyrimidine bases, such as cytosine and thymine, have conjugated double bonds and as such absorb UV light. The photoreaction between adjacent thymine or cytosine bases proceeds at an exceedingly rapid rate (on the order of picoseconds). There are two possible products. The most common is the formation of a cyclobutane ring between the two pyrimidines (Fu et al., 1997, *Applied and Environ Microbiol* 63(4):1551-1556). The other photoproduct is a (6-4) pyrimidone. The formation of these dimers leads to "kinks" within the structure of the DNA inhibiting the formation of proper transcriptional and replicational templates. Cytosine cyclobutane photodimers are susceptible to deamination and can therefore induce point mutations, specifically the CC (two adjacent cytosines) are converted into TT (two adjacent thymines) via the SOS Response system in both eukaryotic and prokaryotic organisms (Fu et al., 2008, *FEMS Microbiol Rev* 32(6):908-26; Eller and Gilchrest; 2000, *Pigment Cell Res* 13 Suppl 8:94-7). The inactivation of specific genes via point mutations is one of the mechanisms of how UV-induced genetic damage can lead to cell death or to the inhibition of cell replication. The inability to form proper replicational and transcriptional templates coupled with the increased number of point mutations leads to the deactivation and inability to reproduce of microorganisms.

DNA, specifically has a maximum absorbency of UV light at 253.7 nm. It has been determined that approximately 26,400 microwatt-seconds/$cm^2$ are needed to deactivate 100% of the most resistant bacteria (Osburne et al., 2010, *Environ Microbiol;* doi:10.1111/j.1462-2920.2010.02203.x).

UV light is separated into 3 distinct categories: UV-A (315-400 nm), UV-B (280-315 nm), and UV-C (200-280 nm) Since DNA optimally absorbs UV light at 253.7 nm, it is UV-C lamps that are used in most prior art germicidal devices. UV devices are used, e.g., to inactivate microorganisms in laboratory settings.

UV radiation is used for disinfection in hospitals, nurseries, operating rooms, cafeterias and to sterilize vaccines, serums, toxins, municipal waste, and drinking waters.

Current steel vessel and container sanitation protocols involve the use of a pressure wash using a hot water cycle to remove pigments, colloidal deposits, and tartrates following wine fermentations. After the hot water cycle, typically the vessels are washed with a 200 mg/L solution of hypochlorite as a sanitation cycle. This is usually followed by a rinse with citric acid. (Boulton et al., Principles and Practices of Winemaking, page 210, Springer, $1^{st}$ Edition, Jan. 15, 1996).

Sodium hypochlorite (NaOCl) is often used for disinfecting hospital wastewater in order to prevent the spread of pathogenic microorganisms, causal agents of nosocomial infectious diseases. Chlorine disinfectants in wastewater react with organic matters, giving rise to organic chlorine compounds such as AOX (halogenated organic compounds adsorbable on activated carbon), which are toxic for aquatic organisms and are persistent environmental contaminants (Bohrerova et al., 2008, *Water Research* 42(12):2975-2982). Other protocols follow the removal of pigments, colloidal deposits, and tartrates with a wash with a caustic solution containing sodium hydroxide (typically 3%) and further followed by a final wash with a citric acid solution (typically 3%) to neutralize any remaining sodium hydroxide. There are several disadvantages to using sodium hydroxide and citric acid for sterilization. The primary disadvantage is the necessary use of large amounts of water as a solvent for both solutions. Any potential water saving measure is of great value both economically and environmentally. Further, the reduction in use of extremely caustic sodium hydroxide would be an added environmental benefit.

Other methods currently used for sterilizing fermentation vessels (made from metals and/or wood) include the use of ozone. Prior to 1997, ozone could only be used for sanitation and purification of bottled drinking water in the United States, and it is widely used around the world for this purpose today. In May 1997, an expert panel assembled by the Electric Power Research Institute (EPR1) declared ozone to be Generally Recognized as Safe (GRAS) for use in food processing in the United States. Since then, wineries have embraced the use of ozone. Its use has been generally accepted and documented to be effective for barrel cleaning and sanitation, tank cleaning and sanitation, clean-in-place systems, and for general surface sanitation. Results have shown the same degree of sanitization as that achieved using caustic for a fraction of the cost and wasted water.

However, in the wine industry, ozone systems tend to be mobile (a single unit can be moved to different vessels), with multiple operators in multiple locations. This makes it important that safety features and ozone management systems be in place and that the system itself be reliable and easy to operate.

Natural levels of ozone range from 0.01 ppm to 0.15 ppm and can reach higher concentrations in urban areas. Ozone is an unstable gas and readily reacts with organic substances. It sanitizes by interacting with microbial membranes and denaturating metabolic enzymes.

Ozone is generated by irradiation of an air stream with ultraviolet (UV) light at a wavelength of 185 nm or by passing dry air or oxygen through a corona discharge (CD technology) generator. For low ozone concentrations (ca. 0.14% by weight, or 0.5 grams per hour), the less expensive UV equipment is sufficient. For more demanding situations where higher ozone concentrations (1.0% to 14% by weight) are required, CD systems are used.

The wine industry is using both CD technology and UV (different from the one described herein). Some manufacturers use multiple UV tubes to achieve a desired level of output. Several manufacturers chose to install air-cooled or water-cooled CD generators in their systems. It is really a question of how much ozone at a certain gallons per minute (gpm) is desired for an application. For clean in place (CIP), 20 gpm may be desired, necessitating a larger system, while only 10 gpm at a lower concentration may provide satisfactory barrel washing.

The Occupational Safety and Health Administration (OSHA) has set limits for ozone exposure in the workplace. These limits are for continuous eight-hour exposure of no more than 0.1 ppm, and a short-term exposure limit (STEL) of 15 minutes at 0.3 ppm, not to be exceeded more than twice per eight-hour work day. Consequently, ozone requires monitoring in the workplace if used for environmental or equipment sanitation using, e.g., ozone.

Ozone is known to have adverse physiological effects on humans (Directorate-General of Labour, the Netherlands 1992, 4(92), 62). Technically, there is no minimum threshold for ozone toxicity. Even low concentrations of ozone produce transient irritation of the lungs as well as headaches. Higher concentrations induce severe eye and upper respiratory tract irritation. Chronic exposure to ozone leads to respiratory tract disease and has been associated with reported increases in tumor growth rates. Exposure to ozone levels greater than the maximum thresholds specified by the American Conference of Governmental Industrial Hygienists (ACGIH)/Occupational Safety and Health Administration (OSHA) results in nausea, chest pain, coughing, fatigue and reduced visual acuity. Thus, while ozone provides an efficient means of sterilization, it also poses an occupational hazard to those involved in the sterilization process.

Another bactericidal chemical frequently used to sterilize fermentation vessels is chlorinated trisodium phosphate (TSP). It has been well established that chlorinated TSP is an effective germicidal agent. TSP, however, is also a severe irritant, capable of inducing contact dermatitis in addition to irritating the respiratory tract (Health Hazard Evaluation Report No. HETA-82-281-1503; HETA-82-281-1503). Also, certain microorganisms, such as *Cryptosporidium*, have developed resistance to reactive chlorine compounds. Further, evidence is mounting that organic chemical byproducts of chemical disinfection, especially byproducts of chlorination, are carcinogens and/or toxins for humans. Thus, expensive filtration devices may be required to remove the chemicals. Further, systems based on filtration require frequent replacement and/or cleaning of the filters. In addition, use of chlorinated TSP requires large quantities of water as a solvent and to extensively rinse the container following chemical sterilization. Also, chlorinated compounds are notorious for causing wine fouling. Thus, chemical disinfection is not a viable alternative when chemical purity of a fluid or alcoholic beverage in a fermentation vessel is desired or required.

Ozone sterilization was originally used to purify blood in the late 1800s. In the 1900s, ozonated water was in use for the treatment of multiple types of disease. In the first World War, ozone was used to treat wounds, gangrene and the effects of poisonous gas. Thus, throughout the time period, toxic and/or carcinogenic chemicals have been used in the sterilization of containers used for fermenting alcoholic beverages.

Using the chemical disinfection or ozone disinfection methods, there is also no established protocol for verifying the level of sterilization achieved by using those methods.

Thus, there is a need in the art for non-toxic and non-carcinogenic methods, systems, and compositions useful for the sterilization of containers, and in particular, for the sterilization of containers for fermenting alcoholic beverages.

The compositions, systems, and methods provided herein meet these and other needs in the art.

BRIEF SUMMARY OF THE INVENTION

The present invention provides compositions, systems, and methods useful for the UV sterilization of containers. In one aspect the invention provides a method for ultraviolet (UV) sterilization of an interior surface of a container. In some embodiments of this method, the method comprises the steps of (a) providing a container having an opening, (b) movably inserting through the opening of the container a first germicidal UV light source, and (c) activating the germicidal UV light source.

Various germicidal UV light sources may be used in the methods of the present invention. In some embodiments, the germicidal UV light source is a pulsed germicidal UV light source.

Various containers can be UV sterilized using a method of the present invention. In some embodiments, the container is a container for fermenting an alcoholic beverage. In some embodiments, the alcoholic beverage is beer or wine.

Microorganisms on the interior surface of the container can be effectively killed using a method of the present invention. In some embodiments, one or more species of microorganisms is present on the interior surface of the container and the activation of the germicidal UV light source results in inhibiting the growth of the one or more species of microorganisms.

Various microorganisms can be killed or growth inhibited using a method of the present invention. In some embodiments, the one or more species of microorganisms is selected from the group consisting of *Candida, Kloeckera, Hanseniaspora, Zygosaccharomyces, Schizosaccharomyces, Torulaspora, Brettanomyces, Saccharomycodes, Pichia, Williopsis, Pediococcus, Lactobacillus*, and *Oenococcus*. In some embodiments, the microorganism is *Lactobacillus*.

The germicidal light source maybe connected to various components within a UV device or UV assembly of the present invention. In some embodiments, the germicidal UV light source is connected to a detector, more specifically, to a UV detector. In some embodiments, the UV detector measures a UV intensity level. In some embodiments, the detector shuts off the germicidal UV light source when a specified UV intensity level is attained.

In some embodiments the germicidal UV source resides in a housing. In some embodiments, a method of the present invention comprises the step of releasing the germicidal UV light source from the housing. In some embodiments, the housing is attached to a bracket covering the dimensions of the container. In some embodiments, a method of the present invention comprises the step of placing the bracket housing the germicidal UV light source on the upper perimeter of the container.

In some embodiments, upon release from the housing, the germicidal UV Light source moves longitudinally into the container to a predetermined position. In some embodiments, upon release from the housing, the germicidal UV Light source moves laterally in the container to a predetermined position. In some embodiments, upon release from the housing, the germicidal UV Light source rotates in the container.

In some embodiments, a method of the present invention comprises the step of movably inserting through the opening of the container a second germicidal UV light source. In some embodiments, the first and second germicidal UV light sources are clustered together. In some embodiments, the first and second germicidal UV light sources are spaced apart.

Using methods of the present invention effective UV sterilization is achieved. In some embodiments, the growth of the one or more species of microorganisms is inhibited by at least 2 log. In some embodiments, the growth of the one or more species of microorganisms is inhibited by at least 3 log. In some embodiments, the growth of the one or more species of microorganisms is inhibited by at least 4 log. In some embodiments, the growth of the one or more species of microorganisms is inhibited by at least 5 log. In some embodiments, the growth of the one or more species of microorganisms is inhibited by at least 6 log.

The present invention also provides for UV devices and for systems using the UV devices. In some embodiments, a UV device comprises a cluster of germicidal UV light sources, an actuator, and a scissor boom. The scissor boom has a first end and a second end. The actuator may be attached to the first end of the scissor boom. The germicidal UV light sources may be attached to the second end of the scissor boom. In some embodiments, the cluster of germicidal UV light sources comprises three germicidal UV light sources.

In some embodiments, the germicidal UV light sources are movably arranged with respect to each other in a vertical configuration. The cluster of germicidal UV light sources may also be connected to a winch. In addition, the cluster of germicidal UV light sources may also be located within a removable housing. Upon removal of the removable housing, the germicidal UV light sources move from the vertical configuration into a tripod configuration. A preferred angle of the tripod configuration is 15 degrees.

Some embodiments of the present invention are set forth in claim format directly below:

1. A method for ultraviolet (UV) sterilization of an interior surface of a container, the method comprising the steps of: (a) providing a container having an opening; (b) movably inserting through the opening of the container a first germicidal UV light source; and (c) activating the germicidal UV light source.

2. The method according to claim 1, wherein the germicidal UV light source is a pulsed germicidal UV light source.

3. The method according to any one of claims 1 to 2, wherein the container is a container for fermenting an alcoholic beverage.

4. The method according to claim 3, wherein the alcoholic beverage is beer.

5. The method according to claim 3, wherein the alcoholic beverage is wine.

6. The method according to any one of claims 1 to 5, wherein one or more species of microorganisms is present on the interior surface of the container and wherein the activation of the germicidal UV light source results in inhibiting the growth of the one or more species of microorganisms.

7. The method according to claim 6, wherein the one or more species of microorganisms is selected from the group consisting of *Candida, Kloeckera, Hanseniaspora, Zygosaccharomyces, Schizosaccharomyces, Torulaspora, Brettanomyces, Saccharomycodes, Pichia, Williopsis, Pediococcus, Lactobacillus*, and *Oenococcus*.

8. The method according to any one of claims 6 to 7, wherein the one or more species of microorganisms is *Lactobacillus*.

9. The method according to any one of claims 6 to 8, wherein the growth of the one or more species of microorganisms is inhibited by at least 2 log.

10. The method according to any one of claims 6 to 9, wherein the growth of the one or more species of microorganisms is inhibited by at least 3 log.

11. The method according to any one of claims 6 to 10, wherein the growth of the one or more species of microorganisms is inhibited by at least 4 log.

12. The method according to any one of claims 6 to 1, wherein the growth of the one or more species of microorganisms is inhibited by at least 5 log.

13. The method according to any one of claims 6 to 12, wherein the growth of the one or more species of microorganisms is inhibited by at least 6 log.

14. The method according to any one of claims 1 to 13, wherein the germicidal UV light source is connected to a detector.

15. The method according to claim 14, wherein the detector measures a UV intensity level.

16. The method according to any one of claims 14 to 15, wherein the detector shuts off the germicidal UV light source when a specified UV intensity level is attained.

17. The method according to any one of claims 1-16, wherein the germicidal UV light source resides in a housing.

18. The method according to claim 17, wherein the housing is attached to a bracket covering the dimensions of the container.

19. The method according to claim 18, further comprising the step of placing the bracket housing the germicidal UV light source on the upper perimeter of the container.

20. The method according to any one of claims 17 to 19, further comprising the step of releasing the germicidal UV light source from the housing.

21. The method according to claim 20, wherein upon release from the housing, the germicidal UV Light source moves longitudinally into the container to a predetermined position.

22. The method according to claim 20, wherein upon release from the housing, the germicidal UV Light source moves laterally into the container to a predetermined position.

23. The method according to claim 20, wherein upon release from the housing, the germicidal UV Light source rotates into the container.

24. The method according to any one of claims 1 to 23 comprising the step of movably inserting through the opening of the container a second germicidal UV light source.

25. The method according to claim 24, wherein the first and second germicidal UV light sources are clustered together.

26. The method according to claim 24, wherein the first and second germicidal UV light sources are spaced apart.

27. A UV device comprising: (i) a cluster of germicidal ultraviolet (UV) light sources, (ii) an actuator, and (iii) a scissor boom having a first end and a second end, wherein the actuator is attached to the first end of the scissor boom and the germicidal ultraviolet (UV) light source is attached to the second end of the scissor boom.

28. The UV device according to claim 27, wherein the germicidal UV light sources are movably arranged to each other in a vertical configuration.

29. The UV device according to any one of claims 27 to 28, wherein the cluster of germicidal UV light sources is connected to a winch.

31. The UV device according to any one of claims 27 to 30, wherein the cluster of germicidal UV light sources is located within a removable housing.

32. The UV device according to any one of claims 27 to 31, wherein the cluster of germicidal UV light sources comprises three germicidal UV light sources.

33. The UV device according to any one of claims 31 to 32, wherein upon removal of the housing, the germicidal UV light sources move from the vertical configuration into a tripod configuration.

BRIEF DESCRIPTION OF THE DRAWINGS

FIG. 1 depicts a schematic diagram of a UV device of the present invention above a container 4, here a cylindrical fermentation vessel. In the UV device shown, a singular mobile cylindrical UV lamp is retracted in a housing 2, here a protective sleeve. A motorized unit 1 is mounted on top of the protective sleeve. The housing 2 is attached to a mounting bracket 3.

FIG. 17 depicts a variety of commercially available UV lamps of different length, shape, and type useful in the present invention (American Air & Water Inc., Hilton Head Island, S.C. 29926, USA). For each UV lamp, the UV-C output is provided in watts and the UV intensity is provided in UV $\mu W/cm^2$ at 1 m. Length as indicated reflects nominal length with standard lamp holders adding 2" overall length. Additional lamp lengths and types are available. *, Ozone is neglible unless noted as OZ for high or VH for very high ozone production.

DETAILED DESCRIPTION OF THE INVENTION

I. Definitions

Figure 2:
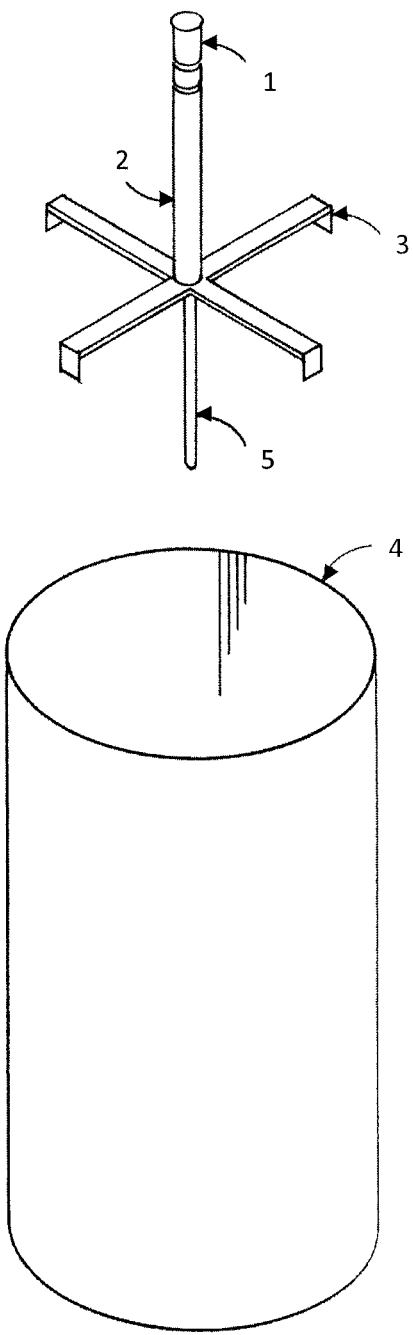
FIG. 2 depicts a schematic diagram of a UV device of the present invention above a container 4, here a cylindrical fermentation vessel. In this embodiment, the UV lamp 5 is being lowered from within a housing 2, here a protective sleeve. The UV lamp 5 can be suspended above the container 4 via a mounting bracket 3. The UV lamp 5 can be raised and lowered by a motorized unit 1 mounted on top of the housing 2.

Throughout the present specification and the accompanying claims the words "comprise" and "include" and variations thereof such as "comprises", "comprising", "includes" and "including" are to be interpreted inclusively. That is, these words are intended to convey the possible inclusion of other elements or integers not specifically recited, where the context allows. No language in the specification should be construed as indicating any non-claimed element essential to the practice of the invention.

The terms "a" and "an" and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximate") one particular value, and/or to "about" (or "approximate") another particular value. When such a range is expressed, another embodiment includes from the one particular value and/or to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that is "less than or equal to the value" or "greater than or equal to the value" possible ranges between these values are also disclosed, as appropriately understood by the skilled artisan. For example, if the value "10" is disclosed the "less than or equal to 10" as well as "greater than or equal to 10" is also disclosed.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

The abbreviations used herein have their conventional meaning within the chemical and biological arts.

As used herein, the term "about" refers to a range of values of plus or minus 10% of a specified value. For example, the phrase "about 200" includes plus or minus 10% of 200, or from 180 to 220, unless clearly contradicted by context.

As used herein, the terms "amount effective" or "effective amount" mean an amount, which produces a desired biological effect. In particular, an effective amount of a UV dosage is an amount, which inhibits the growth of a microorganism by at least 90% (by at least 1 log reduction), by at least 99% (by at least 2 log reduction), by at least 99.9% (by at least 3 log reduction), by at least 99.99% (by at least 4 log reduction), by at least 99.999% (at least 5 log reduction), or by at least 99.9999% (at least 6 log reduction).

As used herein, the term "germicidal lamp" or "germicidal UV lamp" refers to a type of lamp, which produces ultraviolet (UV) light. Short-wave UV light disrupts DNA base pairing causing thymine-thymine dimers leading to death of bacteria and other microorganisms on exposed surfaces.

As used herein, the terms "inhibiting the growth of a microorganism," "inhibiting the growth of a population of microorganisms," "inhibiting the growth of one or more species of microorganisms" or grammatical equivalents thereof refer to inhibiting the replication of one or more microorganisms and may include destruction of the microorganism(s). Assays for determining inhibiting the growth of a microorganism are known in the art and are described herein.

As used herein, the terms "microorganism" or "microbe" comprise a diverse group of microscopic organisms, including, but not limited to, bacteria, fungi, viruses, archaea, and protists.

The terms "optional" or "optionally" as used throughout the specification means that the subsequently described event or circumstance may but need not occur, and that the description includes instances where the event or circumstance occurs and instances in which it does not. The terms also refer to a subsequently described composition that may but need not be present, and that the description includes instances where the composition is present and instances in which the composition is nor present.

As used herein, the terms "sterile" or "sterilization" and grammatical equivalents thereof refer to an environment or an object, which is free of detectable living cells, viable spores, viruses, and other microorganisms.

As used herein, the term "radiation" or grammatical equivalents refer to energy, which may be selectively applied, including energy having a wavelength of between $10^{-14}$ and $10^4$ meters including, for example, electron beam radiation, gamma radiation, x-ray radiation, light such as ultraviolet (UV) light, visible light, and infrared light, microwave radiation, and radio waves. A preferred radiation is UV light radiation. "Irradiation" refers to the application of radiation to a surface.

As used herein the term "ultraviolet" and the abbreviation "UV" refer to electromagnetic radiation with wavelengths shorter than the wavelengths of visible light and longer than those of X rays. UV part of the light spectrum is situated beyond the visible spectrum at its violet end.

As used herein, the abbreviation "UV-A" refers to ultraviolet light in the range of 315-400 nanometers (nm).

As used herein, the abbreviation "UV-B" refers to ultraviolet light in the range of 280-315 nanometers (nm).

As used herein, the abbreviation "UV-C" refers to ultraviolet light in the range of 200-280 nanometers (nm).

As used herein, the term "UV dose" refers to the amount of UV irradiation absorbed by an exposed population of microbes, typically in units of $mJ/cm^2$ ($mJ/cm^2$=1,000 $\mu W/cm^2$ per second).

As used herein, the terms "UV intensity" or "UV irradiance" refer to the irradiance field of a UV germicidal irradiation system, i.e., the total radiant energy incident on a surface from all directions. It is measured in $\mu W/cm^2$ at 1 m. The UV intensity greatly depends on the distance from the UV emitter and the transmittance of the medium.

The term "ultraviolet radiation" or "UV radiation" refers to radiation having a wavelength or wavelengths between from 160 to 400 nm. If a range is specified, a narrower range of radiation is meant within the 160 to 400 nm range. The range specified, unless otherwise indicated, means radiation having a wavelength or wavelengths within this specified range.

The present invention generally relates to compositions, systems and methods for ultraviolet (UV) disinfection, and more specifically, to compositions, systems and methods for UV disinfection of a container, and more particularly to compositions, systems and methods for UV disinfection of a container used in the process of fermentation for an alcoholic beverage. A system as described herein comprises at least a UV device and a container.

II. UV Devices

Figure 3:
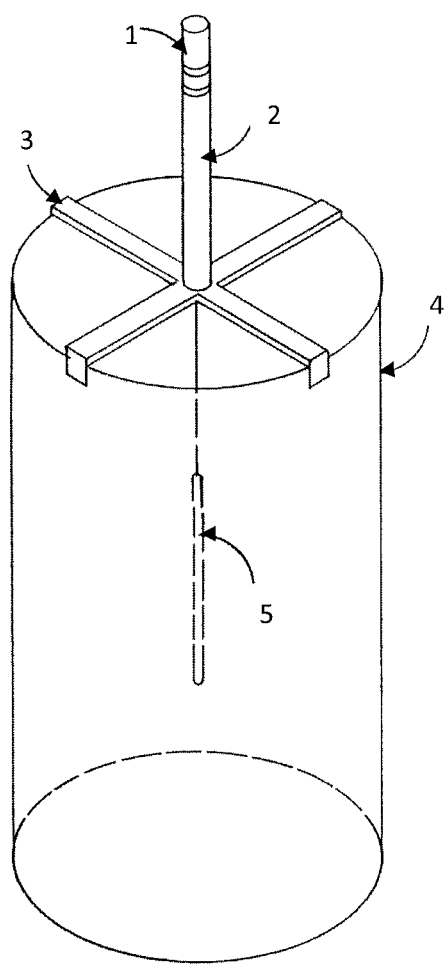
FIG. 3 depicts a schematic diagram of a UV device of the present invention placed on a container 4, here a cylindrical fermentation vessel. In this embodiment, the UV lamp 5 is being lowered into the interior of the container 4. The UV device is supported by a mounting bracket 3. The UV lamp is being lowered from a housing 2, here a protective sleeve, by a motorized unit 1 mounted on top of the housing 2.
Figure 4:
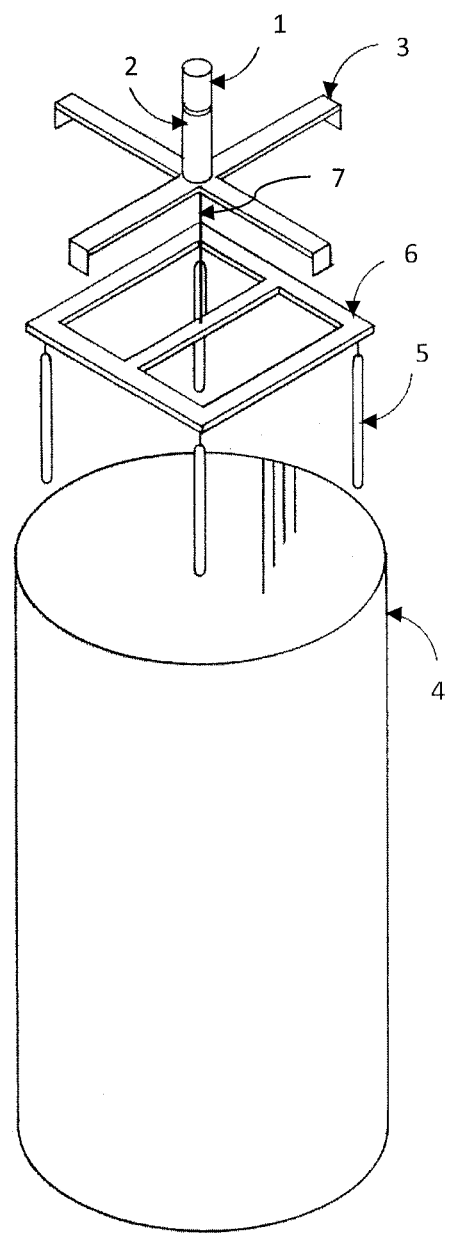
FIG. 4 depicts a schematic diagram of a UV device of the present invention comprising four UV lamps 5 mounted on a frame 6, which can be attached to a motorized unit 1 by a rigid rod or flexible cable 7. In this embodiment, four UV lamps were chosen as an example to demonstrate that the use of more than one UV lamp 5 in various un-clustered positions is encompassed by the present invention. In this embodiment, the UV lamps 5 are being lowered into the interior of the container 4, here a cylindrical fermentation vessel. The UV device is supported by a mounting bracket 3. The cable or rigid rod 7 supporting the frame 6 is lowered from within a housing 2, here a protective sleeve, by a motorized unit 1 mounted on top of the housing 2.
Figure 5:
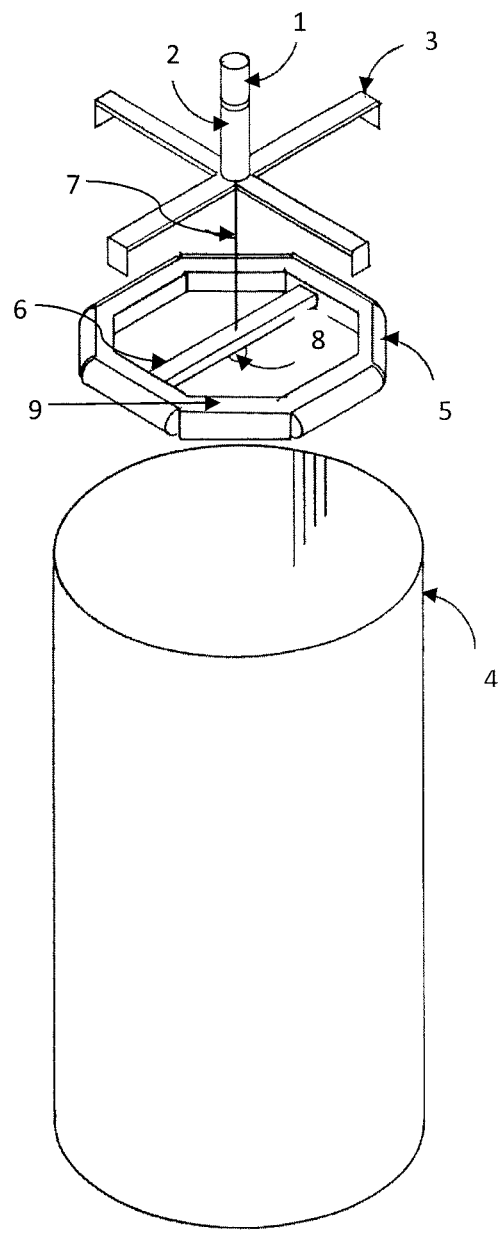
FIG. 5 depicts a schematic diagram of a UV device of the present invention showing a different configuration of UV lamps 5. In this embodiment, eight UV lamps 5 are mounted on an octagonal bracket 9, which can be attached to a motorized unit 1 by a rigid rod or flexible cable 7. In this figure, the UV lamps 5 are being lowered into the interior of the container 4, here a cylindrical fermentation vessel. The UV device is supported by a mounting bracket 3. The cable or rigid rod 7 attached to a connecting plate 6 is lowered from within a housing 2, here a protective sleeve, by a motorized unit 1 mounted on top of the housing 2. An additional UV lamp 8 may optionally be placed at the bottom of the connecting plate 6. The UV lamp 8 will be attached to a position on the connecting plate 6 such that the lower surface of the container 4 will receive sufficient UV radiation to kill or inhibit the growth of all desired microorganisms by the end of the sterilization cycle. In another embodiment, a reflective lid is positioned horizontally between the octagonal bracket 9 and the UV lamp 8 may be fixed to the surface of the octagonal bracket 9 to increase the intensity of UV light directed at the lower surface and pointing downwards to ensure the bottom surface of the container 4 is exposed to sufficient UV radiation.
Figure 6:
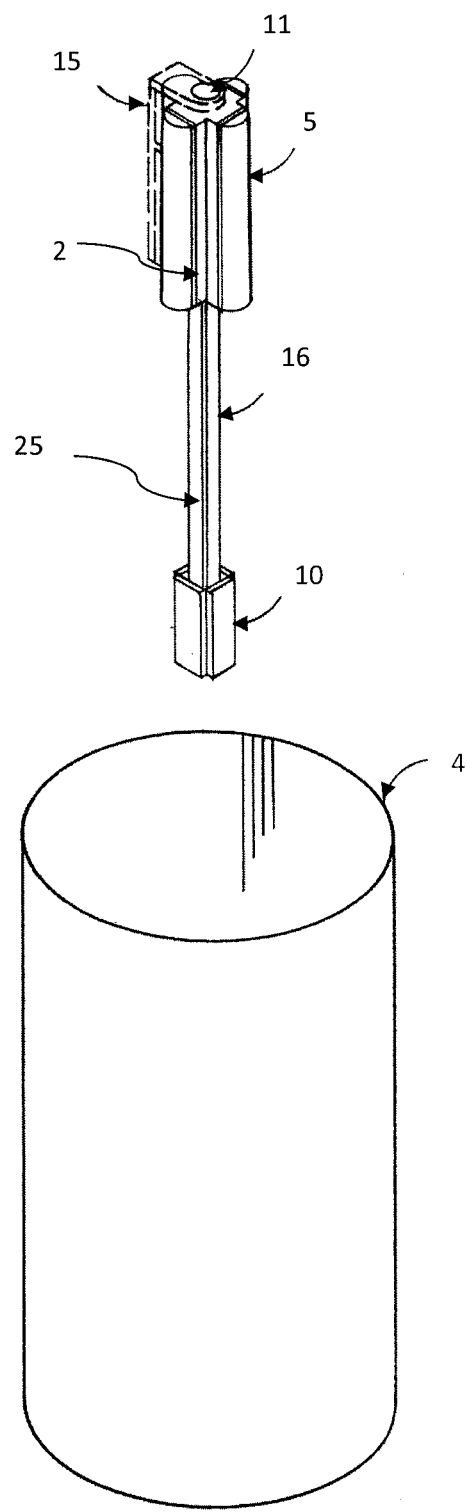
FIG. 6 depicts a schematic diagram of a UV device of the present invention showing a different configuration of UV lamps 5. The UV device is supported by a folding base plate 10, which is attached to a central post 16 having a track 25. The device is inserted through the top opening of a container 4, here a cylindrical fermentation vessel. The intensity of the UV radiation is monitored by a UV detector 1, which optionally is attached to an adjustable bracket 15 allowing the detector 1 to be placed as close to the inner surface of the container 4 as possible. The UV lamps 5 are optionally covered in this configuration by an acrylic covering that does not absorb UV-C light. The lamps 5 are supported by a housing 2, which as shown in FIG. 7 may fold open. The position and angle of the lamps 5 may be adjusted as depicted in FIG. 7.
Figure 7:
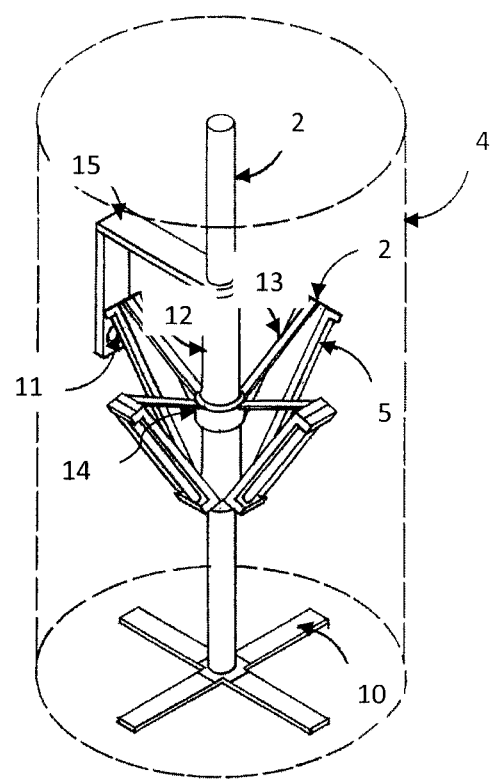
FIG. 7 depicts a schematic diagram of a UV device of the present invention showing a different configuration of UV lamps 5. The UV device is supported by a folding base plate 10. The UV device is inserted through the top opening of a container 4, here a cylindrical fermentation vessel. The UV lamps 5 are held in housings 2, which fold open. The housings 2 are attached to a central sleeve 12 via connecting rods 13. The position of the central sleeve 12 may be adjusted to adjust the angle that the UV lamps 5 protrude from the central axis. In this embodiment, the central sleeve 12 is mounted in turn on another centrally mounted motorized sleeve 14, which can move the entire UV device up and down within the container 4. The intensity of the UV radiation is monitored by a UV detector 1, which is attached to an adjustable bracket 15 allowing the detector 1 to be placed as close to the inner surface of the container as possible. The angling of the lamps 5 also ensures the base of the container is irradiated with UV.
Figure 8:
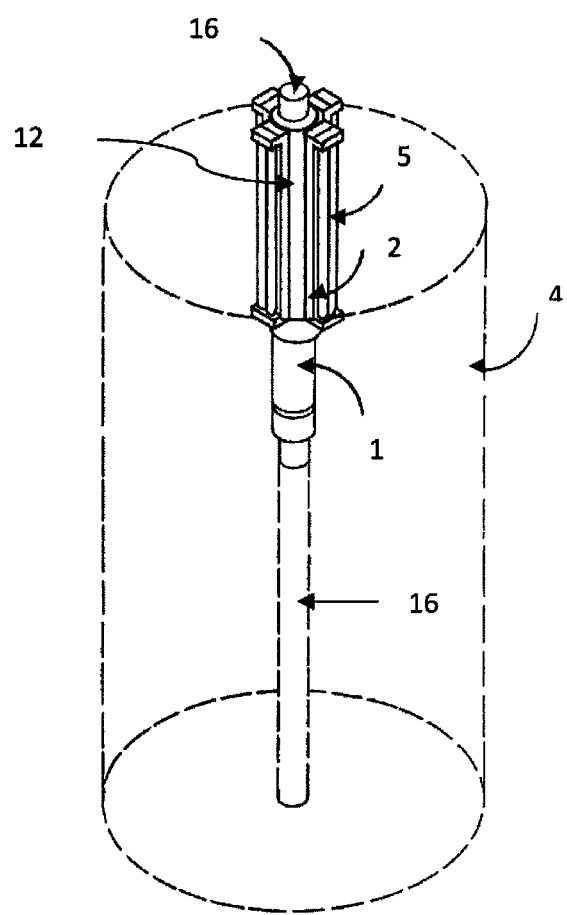
FIG. 8 depicts a schematic diagram of a UV device of the present invention showing a different configuration of UV lamps 5. In this embodiment, four UV lamps 5 mounted in housings 2 are mounted to a central sleeve 12, which can be moved up and down within the container 4, here a cylindrical fermentation vessel, on a central post 16, via a motorized unit 1 attached to the central sleeve 16. The lamp housings 2 are affixed to two parallelogramming arms (not shown in this Figure, shown in FIG. 9), which can move in a circular motion and adjust the position of the UV lamps 5 and their proximity to the inner surface of container 4 of varying diameter.
Figure 9:
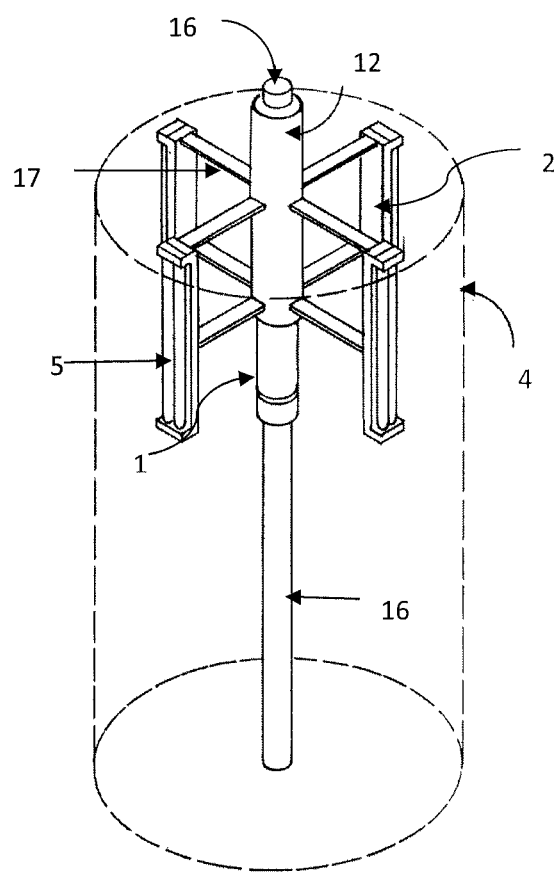
FIG. 9 depicts a schematic diagram of a UV device of the present invention showing a different position of UV lamps 5 (same as FIG. 8, but with UV lamps 5 extended). In this embodiment, four UV lamps 5 mounted in housings 2 are mounted to a central sleeve 12, which can be moved up and down within the container 4, here a cylindrical fermentation vessel on a central post 16, via a motorized unit 1 attached to the central sleeve 16. The lamp housings 2 are affixed to two parallelogramming arms 17, which can move in a circular motion and adjust the position of the UV lamps 5 and their proximity to the inner surface of containers 4 of varying diameter. In this figure the parallelogramming arms 17 are shown fully extended. Arms 17 may also not be fully extended, i.e., form they an angle between 0 and 90 degrees and be positioned within the closed position (shown in FIG. 8) and the open position (shown in FIG. 9).
Figure 10:
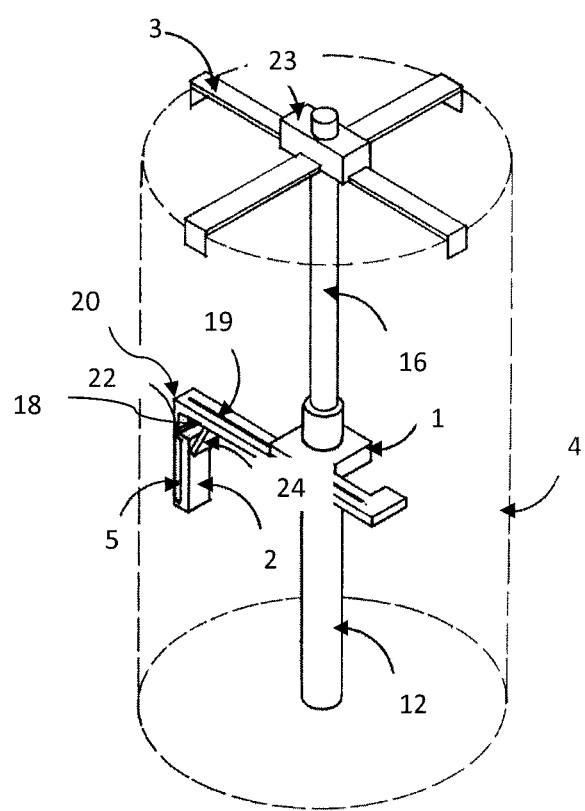
FIG. 10 depicts a schematic diagram of a UV device of the present invention showing a different configuration using a pulsed UV lamp 5. In this embodiment, the pulsed UV lamp 5 is shown within a housing 2, which contains a fan cooling system (not shown) in order to maintain the lamp temperature within an optimal range. The entire UV device is supported by a bracket 3, mounted on top of the container 4, here a cylindrical fermentation vessel. The assembly holding the UV lamp 5 is attached via an arm 18, with a track 19, that allows the position of the UV light to be adjusted horizontally via a motorized unit 1. The positioning of the UV pulsed lamp 5 can be optimized by a range-finding device 20 (also referred to as a guide) mounted at position 22. The motorized unit 1 can also move up and down a central sleeve 12, adjusting the position vertically. Central sleeve 12 also moves up and down on central post 16, and can telescope up covering central post 16 in order to decrease the overall size of the device facilitating transport. Motor unit 23 mounted at the top of the central post 16 spins the central post 16 enabling the pulsed UV lamp 5 to irradiate the entire surface of the container 4 (by moving vertically and rotating). Adjusting bracket 24 can adjust the position of the pulsed UV lamp 5 from vertical to horizontal (shown in FIG. 11) by moving along a track 19 at the bottom of an 18.
Figure 11:
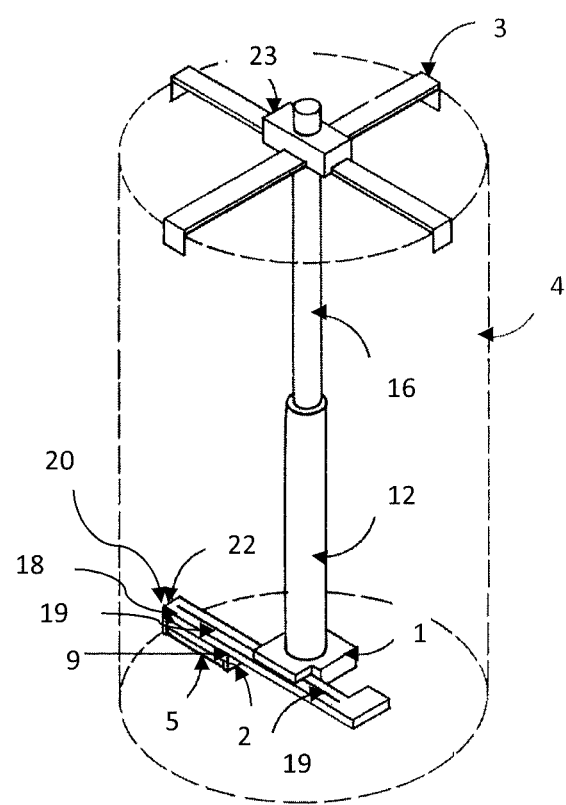
FIG. 11 depicts a schematic diagram of a UV device of the present invention showing a different position using a pulsed UV lamp 5 (same as embodiment as FIG. 10, but with UV lamps 5 in horizontal position). In this embodiment, the pulsed UV lamp 5 is shown within a housing 2, which contains a fan cooling system (not shown) in order to maintain the lamp temperature within an optimal range. The UV device is supported by a bracket 3 placed or mounted on top of a container 4, here a cylindrical fermentation vessel. The assembly holding the UV lamp 5 is attached via an arm 18, with a track 19, that allows the position of the UV light to be adjusted horizontally via a motorized unit 1. The positioning of the UV pulsed lamp 5 can be optimized by range-finding device 20 mounted at position 22. The motorized unit 1 can also move up and down a central sleeve 12 adjusting the position vertically. Central sleeve 12 also moves up and down on central post 16 and can telescope up covering central post 16 in order to decrease the overall size of the device facilitating transport. Motor unit 23 mounted at the top of the central post 16 spins the central post 16 enabling the pulsed UV lamp 5 to irradiate the entire surface of the container 4 (by moving vertically and rotating). Adjusting bracket 24 (hidden) can adjust the position of the pulsed UV lamp 5 from vertical to horizontal (shown in FIG. 12) by moving along a track 19 at the bottom of arm 18. In the embodiment shown, the UV lamp 5 is held horizontally allowing the of the vessel to be bottom surface of the vessel to be irradiated with pulsed UV light.
Figure 12:
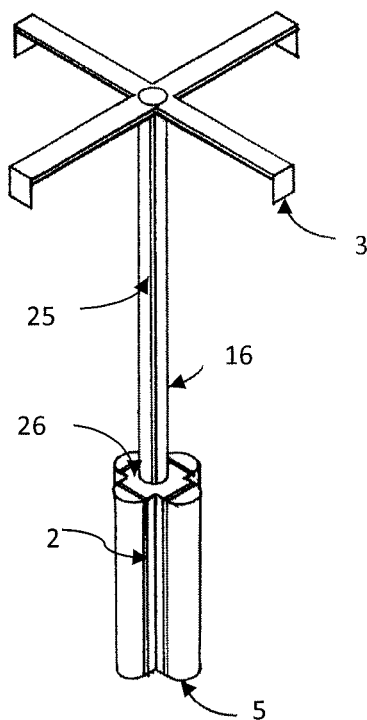
FIG. 12 depicts a schematic diagram of a UV device of the present invention showing a different configuration using four clustered UV lamps 5. In this embodiment, the UV lamps 5 are mounted to a housing 2 (the housing may or may not have reflectors of various cross sections e.g. parabolic, elliptical, or circular). The UV device is supported to the top of a container (not shown) by a four-armed bracket 3. The clustered UV lamps 5 can move up and down a central post 16 along a track 25. This is accomplished by a motorized unit (not shown here) located between the clustered UV lamps 5 in position 26.
Figure 13:
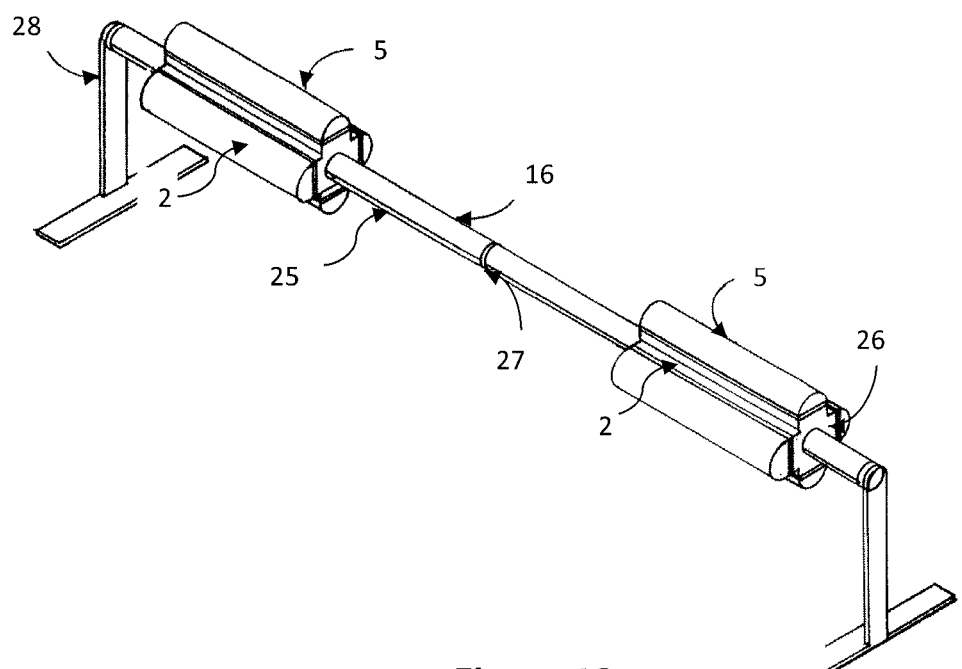
FIG. 13 depicts a schematic diagram of a UV device of the present invention showing a different configuration using two sets of four clustered UV lamps 5. In this embodiment, the UV lamps 5 are mounted to a housing 2 (the housing may or may not have reflectors of various cross sections e.g. parabolic, elliptical, or circular). This embodiment is preferred for use within a horizontal container. The UV device is supported to the top of a container (not shown) by a horizontal stand 28 The clustered UV lamps 5 can move horizontally along a central post 16 along a track 25. This is accomplished by a motorized unit located between the clustered lamps in position 26. The central post 16 is telescoping allowing one half to slide into the other at position 27. This allows the length of the UV device to be adjusted to the length of the container. Two clusters of UV lamps 5 are shown to demonstrate that more than one cluster of UV lamps 5 can be used.
Figure 14:
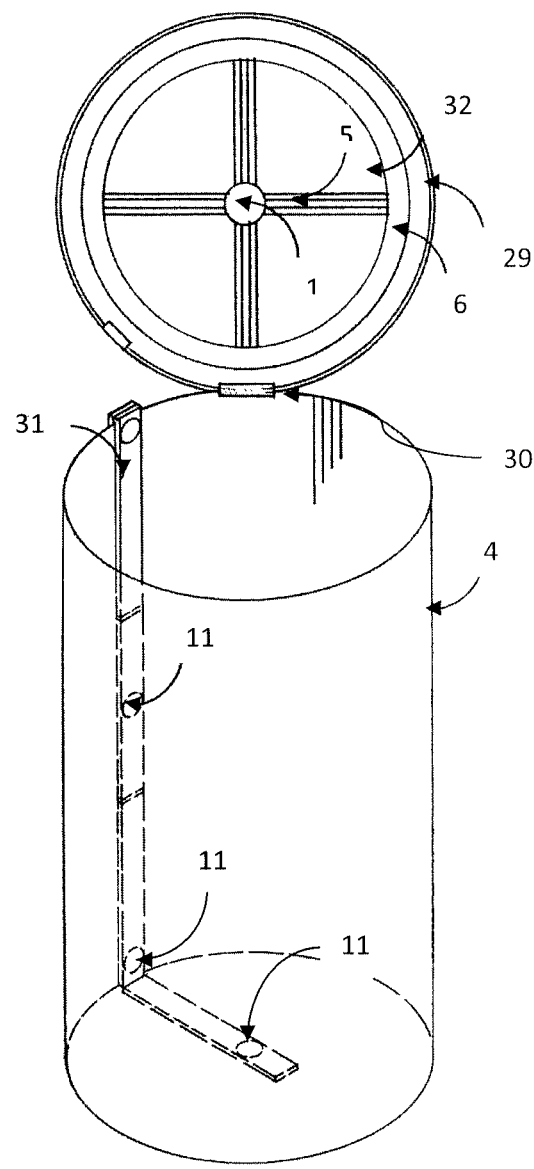
FIG. 14 depicts a schematic diagram of a UV device of the present invention showing a different configuration of UV lamps 5. In this embodiment, the UV lamps 5 are mounted on a lid 29, such as a hinged lid 30, to a container 4, here a cylindrical fermentation vessel. A removable bracket 31 providing support for a system comprising one or more UV detectors 11 is mounted along the inner surface of the container 4. These UV detectors 11 ensure sufficient intensity of UV radiation required to kill or inhibit growth of unwanted microorganisms has reached all interior surfaces of the container 4. In this embodiment, the UV lamps 5 are mounted to frame 6 and lowered via a cable 7 (not shown, shown in FIG. 15) attached to a motorized unit 1. A reflector 32 may optionally be mounted to the lower surface of the lid 29.
Figure 15:
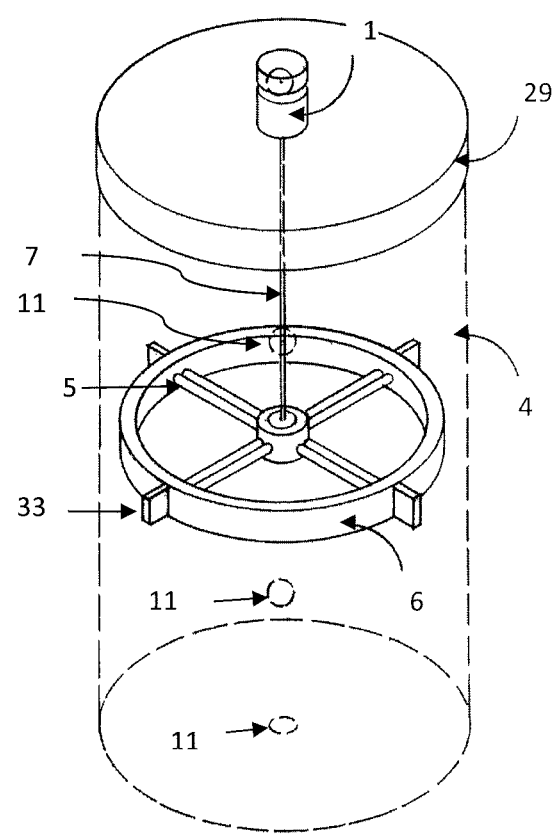
FIG. 15 depicts a schematic diagram of a UV device of the present invention showing a different position of UV lamps 5 (same embodiment as FIG. 14 but now with the frame 6 and UV lamps 5 lowered). A removable bracket 31 (not shown here, shown in FIG. 14) providing support for a system comprising one or more UV detectors 11 (shown in FIG. 14) is mounted along the inner surface of the container 4. These UV detectors 11 ensure sufficient intensity of UV radiation required to kill or inhibit growth of unwanted microorganisms has reached all surfaces of the container 4. In this embodiment, the UV lamp assembly is guided down the container 4 by nylon blocks 33 attached to frame 6. The lowering of the UV lamp assembly occurs via a motorized unit 1, to which the UV lamp assembly is attached via a cable 7. The lowering of the UV lamp assembly is optional. It can remain at the top of the vessel situated just below the lid 29. In some embodiments, the motorized unit moves the UV lamp assembly in a circular manner.
Figure 16:
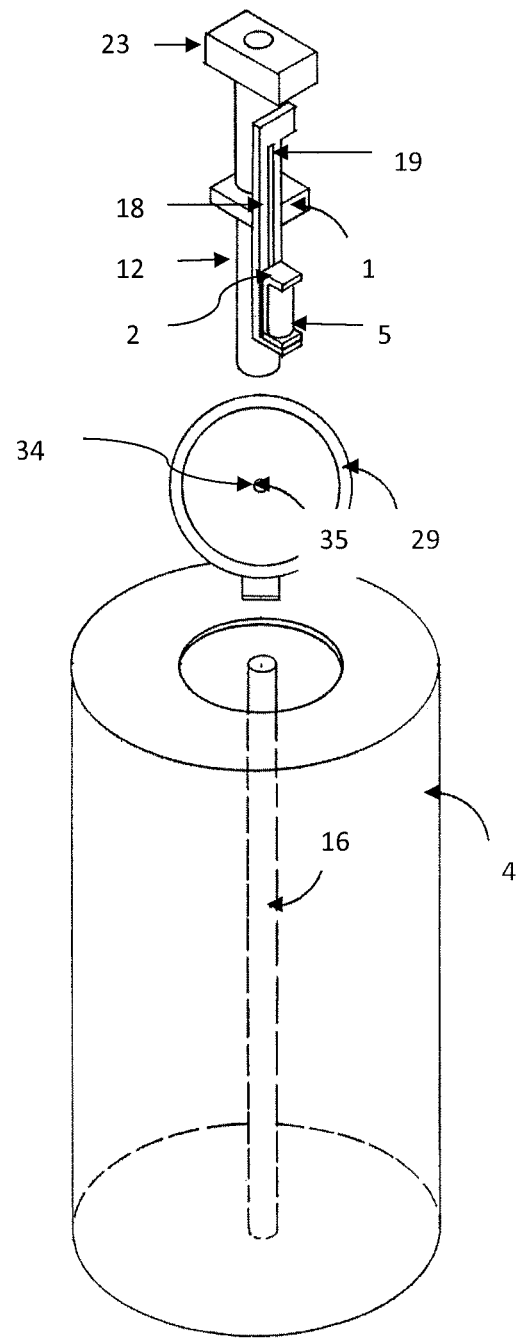
FIG. 16 depicts a schematic diagram of a UV device of the present invention showing a different configuration of a pulsed UV lamp 5. The pulsed UV lamp 5 is shown within a housing 2, which contains a fan cooling system (not shown) in order to maintain the lamp temperature within an optimal range. The assembly holding the UV lamp 5 (e.g., a pulsed UV lamp) attached via an arm 18 with a track 19 that allows the position of the UV lamp 5 to be adjusted horizontally via a motorized unit 1. The motorized unit 1 can also move up and down a central sleeve 12 adjusting the position vertically. Central sleeve 12 also moves up and down on central post 16 that can be a permanent integral component of the container 4, here a cylindrical fermentation vessel. Motor unit 23 mounted at the top of the central sleeve 12 spins the central sleeve 12 enabling the pulsed UV lamp 5 to irradiate the entire surface of the container (by moving vertically and rotating). The assembly holding the UV lamp 5 is attached via an arm 18 with a track 19 that allows the position of the UV lamp 5 to be adjusted horizontally via a motorized unit 1. A post or boss 34 at position 35 further enhances the stability of central post 16 once the UV device is mounted and lid 29 is closed.
Figure 18A:
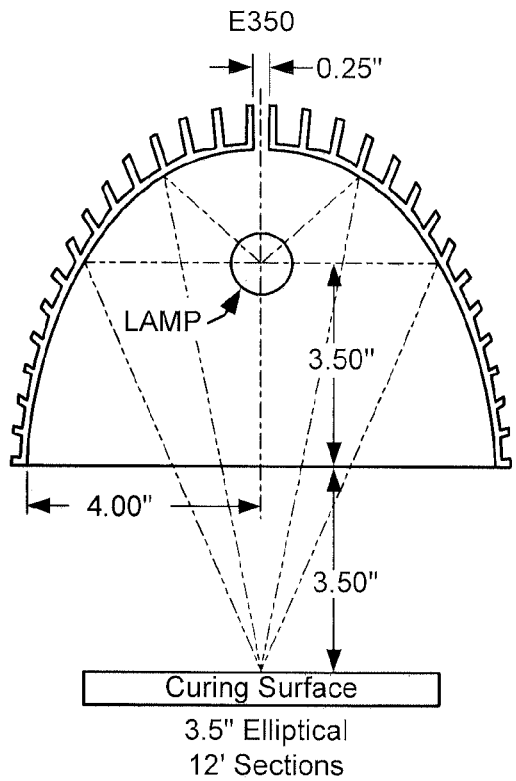
FIG. 18 depicts the cross section of four commercially available reflectors (Hill Technical Sales Corp.) for use in the present invention. The upper two cross sections of the reflectors shown in (A) and (B) are elliptical and provide a line source of UV light. One focal point of the ellipse is located at the center of the UV lamp the other focal point is positioned approximately 1.75" or 3.5" (depending on reflector used) from the bottom edge of the reflector to the surface being irradiated. The lower two cross sections of the reflectors shown in (C) and (D) are parabolic and provide a collimated UV radiation source. The reflectors bottom edge preferably are located 4 to 5 inches from the surface being irradiated.
Figure 18B:
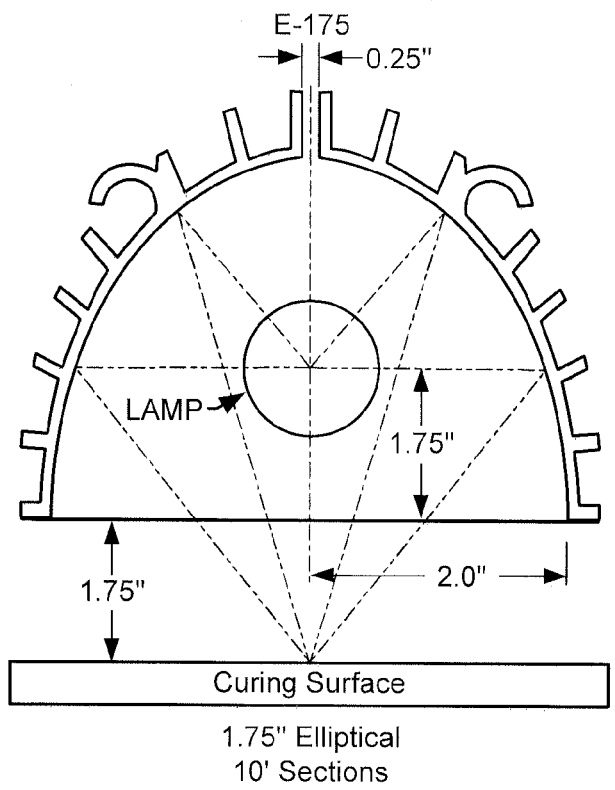
Figure 18C:
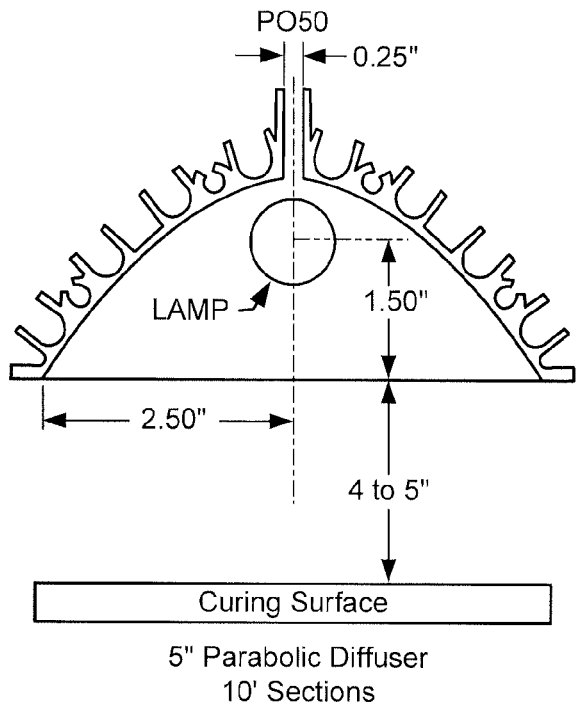
Figure 18D:
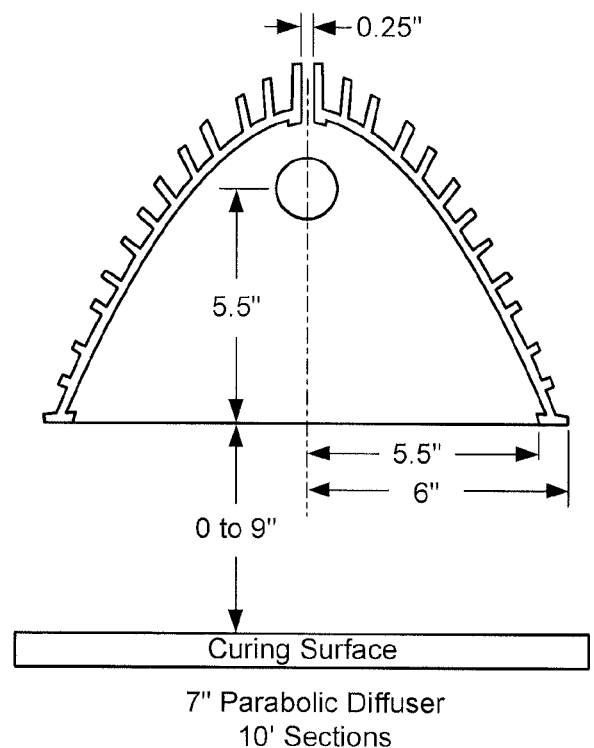
Figure 19A:
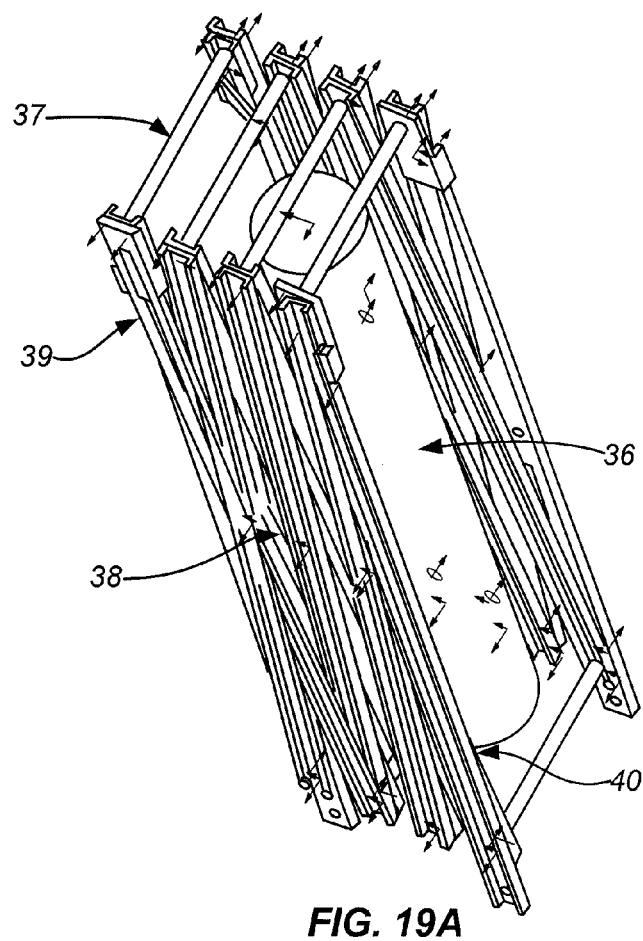
FIG. 19 depicts an embodiment of a UV device of the present invention referred to as linear actuator or scissor boom in two configurations: (A), scissor boom folded; (B), scissor boom extended. A UV lamp cluster housing 36 is attached to the outer end of the scissor boom. The UV lamp cluster housing houses a cluster of UV lamps (41, not shown in Figure). A linear actuator 37 pushes a scissor mechanism 38 up and down a first slide rail 39 located at the inner end (first end) of the scissor boom and allows the length of the scissor boom to be varied according to the diameter of the container into which it is inserted and/or mounted to. A second sliding rail 40, located at the outer end (second end) of the scissor boom allows the scissor boom to expand and contract in length. Once in place, the UV lamp cluster 40 (not shown in Figure) is dropped from its UV lamp cluster housing 36 and lowered down the central axis of the container. Arrows indicate pivot points. A sensor, e.g., range-finding device (not shown in Figure) may also be attached to the second end of the scissor boom and will determine the length to which the scissor boom expands.

The present invention describes a variety of UV devices. In some embodiments of the present invention, a UV device is a UV device as depicted in FIG. 1, 2 or 3. In some embodiments of the present invention, a UV device is a UV device as depicted in FIG. 4. In some embodiments of the present invention, a UV device is a UV device as depicted in FIG. 5. In some embodiments of the present invention, a UV device is a UV device as depicted in FIG. 4. In some embodiments of the present invention, a UV device is a UV device as depicted in FIG. 6 or 7. In some embodiments of the present invention, a UV device is a UV device as depicted in FIG. 8 or 9. In some embodiments of the present invention, a UV device is a UV device as depicted in FIG. 10. In some embodiments of the present invention, a UV device is a UV device as depicted in FIG. 11. In some embodiments of the present invention, a UV device is a UV device as depicted in FIG. 12. In some embodiments of the present invention, a UV device is a UV device as depicted in FIG. 13. In some embodiments of the present invention, a UV device is a UV device as depicted in FIG. 14 or 15. In some embodiments of the present invention, a UV device is a UV device as depicted in FIG. 16. In some embodiments of the present invention, a UV device is a UV device as depicted in FIG. 19. In some embodiments of the present invention, a UV device is a UV device as depicted in FIG. 20.

The UV devices described herein and which are used in the methods described herein are not connected to or connected with or connectable to a container.

In some embodiments, a UV device comprises a UV light source, also referred to as UV lamp.

Notably, any number of UV lamps including low pressure, medium pressure, high pressure, and ultra high-pressure lamps, which are made of various materials, e.g., most commonly mercury (Hg) can be used with the system configuration according to the present invention and in the methods described herein. Additionally, spectral calibration lamps, electrodeless lamps, and the like can be used.

A. Germicidal UV Light Source

Ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, UV light, and in particular, UV-C light is "germicidal," i.e., it deactivates the DNA of microorganism, such as bacteria, viruses and other pathogens and thus, destroys their ability to multiply and cause disease, effectively resulting in sterilization of the microorganisms. While susceptibility to UV light varies, exposure to UV energy for about 20 to about 34 milliwatt-seconds/$cm^2$ is adequate to deactivate approximately 99 percent of the pathogens. In some embodiments of the present invention, a UV light source is a germicidal UV light source. A UV light source, also referred to herein as UV lamp, is indicated in the drawings and respective legends as 5.

1. Pulsed Germicidal UV Light Source

In some embodiments of the present invention, a germicidal UV light source is a pulsed germicidal UV light source. Pulsed UV light is composed of a wide spectrum of light ranging from the UV region to the infrared (Wang and MacGregor, 2005, *Water Research* 39(13):2921-25). A large portion of the spectrum lies below 400 nm and as such has germicidal properties. Pulsed UV light has proven equally if not more effective (same sterilization levels achieved more rapidly) at sterilizing surfaces when compared with traditional germicidal UV-C lights (Bohrerova et al., 2008, *Water Research* 42(12):2975-2982). In a pulsed UV system, UV-light is pulsed several times per second, each pulse lasting between 100 ns (nano second) and 2 ms. An additional advantage of a pulsed UV light system is that it obviates the need for the toxic heavy metal mercury, which is used in traditional germicidal UV lamps. A pulsed UV system requires less power than a mercury UV lamp and as such, is more economical.

The peak intensity of a pulsed UV lamp is typically one to two orders of magnitude higher than that of a mercury UV lamp of similar wattage. These high peak energies are achieved by storing energy in the high voltage storage capacitor and releasing this energy in a very short burst through the flash lamp. Pulse widths of 10 μs (micro second) to 300 μs are common in today's industrial flashlamp systems. Peak energy levels range from 300 kilowatts to over a megawatt. (Kent Kipling Xenon Corporation Wilmington, Mass.). Sterilization is achieved because the intensity of the light produced by the pulsed lamp is greater than that of conventional UV-C lamps. Further, pulsed UV achieves sterilization via the rupture and disintegration of micro-organisms caused by overheating following absorption UV photons emitted in the light pulse (Wekhof et al., "Pulsed UV Disintegration (PUVD): a new sterilization mechanism for packaging and broad medical-hospital applications." The First International Conference on Ultraviolet Technologies. Jun. 14-16, 2001; Washington, D.C., USA).

2. Low Pressure UV Lamp

In some embodiments of the present invention, a germicidal UV light source is a low pressure UV lamp. Low-pressure UV lamps are very similar to a fluorescent lamp, with a wavelength of 253.7 nm. Low pressure lamps are most effective, because they emit most of the radiant energy in the germicidal wavelength of 253.7 nm also known as the UV-C part of the spectrum. This is why low pressure lamps are mostly used in germicidal UV applications. The most common form of germicidal lamp looks similar to an ordinary fluorescent lamp but the tube contains no fluorescent phosphor. In addition, rather than being made of ordinary borosilicate glass, the tube is made of fused quartz. These two changes combine to allow the 253.7 nm UV light produced by the mercury arc to pass out of the lamp unmodified (whereas, in common fluorescent lamps, it causes the phosphor to fluoresce, producing visible light). Germicidal lamps still produce a small amount of visible light due to other mercury radiation bands. In some embodiments, a low pressure UV lamp looks like an incandescent lamp but with the envelope containing a few droplets of mercury. In this design, the incandescent filament heats the mercury, producing a vapor which eventually allows an arc to be struck, short circuiting the incandescent filament. Some low pressure lamps are shown in FIG. 17. Each of those low pressure UV lamp can be used in the present invention.

3. Medium and High Pressure UV Lamps

In some embodiments of the present invention, a germicidal UV light source is a medium-pressure UV lamp. Medium-pressure UV lamps are much more similar to high-intensity discharge (HID) lamps than fluorescent lamps. Medium-pressure UV lamps radiate a broad-band UV-C radiation, rather than a single line. They are widely used in industrial water treatment, because they are very intense radiation sources. They are as efficient as low-pressure lamps. A medium-pressure lamps typically produces very bright bluish white light. In some embodiments of the present invention, a germicidal UV light source is a high pressure UV lamp.

4. Dimension of Germicidal UV Light Source

Different sized and shaped UV lamp sources may be used depending on the shape of the container and the desired duration of the sterilization cycle. In some embodiments, a longer and more powerful UV lamp will provide for shorter duration cycles.

In some embodiments of the present invention, the UV light source is a UV-C lamp of 64" in length with an output of 190 microwatts/cm² at 254 nm (American Air and Water®, Hilton Head Island, S.C. 29926, USA). Other useful UV-C lamps for use in the systems and methods of the present invention are shown in FIG. 17.

In some embodiments of the present invention, a germicidal UV lamp is a hot cathode germicidal UV lamp, examples of which are shown in FIG. 17.

In some embodiments of the present invention, a germicidal UV lamp is a slimline germicidal UV lamp, examples of which are shown in FIG. 17.

In some embodiments of the present invention, a germicidal UV lamp is a high output germicidal UV lamp, examples of which are shown in FIG. 17.

In some embodiments of the present invention, a germicidal UV lamp is a cold cathode germicidal UV lamp, examples of which are shown in FIG. 17.

5. Power Output and UV Intensity of Germicidal UV Light Sources

UV disinfection is a photochemical process. The effectiveness of UV-C is directly related to intensity and exposure time. Environmental factors, such as, air flow, humidity, airborne mechanical particles and distance of microorganism to the UV light source can also affect the performance of a UV device. While those environmental factors when present make it somewhat difficult to calculate the effective UV dosage required to kill or to inhibit the growth of a microorganism of interest, it has been shown that UV light will kill or inhibit the growth of any microorganism given enough UV dosage.

For UV disinfection and sterilization, the microorganisms present in a container are exposed to a lethal dose of UV energy. UV dose is measured as the product of UV light intensity times the exposure time within the UV lamp array. The microorganisms are exposed for a sufficient period of time to a germicidal UV light source in order for the UV rays to penetrate the cellular membrane and breaking down the microorganisms' genetic material. The following tables provide the approximate required intensities to kill or growth inhibit ("Kill Factor") either 90% or 100% of microorganisms (American Water & Air® Inc., Hilton Head Island, S.C. 29926, USA):

Table 1 provides the approximate required intensities to kill or growth inhibit ("Kill Factor") either 90% or 99% of mold spores (American Water & Air® Inc., Hilton Head Island, S.C. 29926, USA):

| Mold Spores | Energy Dosage of UV Radiation (UV Dose) in μWs/cm² Needed for Kill Factor | |
| --- | --- | --- |
| | 90% (1 log Reduction) | 99%* (2 log Reduction) |
| *Aspergillius flavus* | 60,000 | 99,000 |
| *Aspergillius glaucus* | 44,000 | 88,000 |
| *Aspergillius niger* | 132,000 | 330,000 |
| *Mucor racemosus* A | 17,000 | 35,200 |
| *Mucor racemosus* B | 17,000 | 35,200 |
| *Oospora lactis* | 5,000 | 11,000 |

-continued

| Mold Spores | Energy Dosage of UV Radiation (UV Dose) in µWs/cm² Needed for Kill Factor | |
|---|---|---|
| | 90% (1 log Reduction) | 99%* (2 log Reduction) |
| Penicillium expansum | 13,000 | 22,000 |
| Penicillium roqueforti | 13,000 | 26,400 |
| Penicillium digitatum | 44,000 | 88,000 |
| Rhisopus nigricans | 111,000 | 220,000 |

*it is noted that American Ultraviolet Company (Lebanon, IN, USA) states that the energy dosage of UV radiation (UV Dose) shown above to kill 99% of the indicated mold spores, is sufficient to achieve a 100% kill factor of the indicated mold spores.

Table 2 provides the approximate required intensities to kill or growth inhibit ("Kill Factor") either 90% or 99% of bacteria (American Water & Air® Inc., Hilton Head Island, S.C. 29926, USA):

| Bacteria | Energy Dosage of UV Radiation (UV Dose) in µWs/cm² Needed for Kill Factor | |
|---|---|---|
| | 90% (1 log Reduction) | 99%* (2 log Reduction) |
| Bacillus anthracis - Anthrax | 4,520 | 8,700 |
| Bacillus anthracis spores - Anthrax spores | 24,320 | 46,200 |
| Bacillus magaterium sp. (spores) | 2,730 | 5,200 |
| Bacillus magaterium sp. (veg.) | 1,300 | 2,500 |
| Bacillus paratyphusus | 3,200 | 6,100 |
| Bacillus subtilis spores | 11,600 | 22,000 |
| Bacillus subtilis | 5,800 | 11,000 |
| Clostridium tetani | 13,000 | 22,000 |
| Corynebacterium diphtheriae | 3,370 | 6,510 |
| Ebertelia typhosa | 2,140 | 4,100 |
| Escherichia coli | 3,000 | 6,600 |
| Leptospira canicola - infectious Jaundice | 3,150 | 6,000 |
| Microccocus candidus | 6,050 | 12,300 |
| Microccocus sphaeroides | 1,000 | 15,400 |
| Mycobacterium tuberculosis | 6,200 | 10,000 |
| Neisseria catarrhalis | 4,400 | 8,500 |
| Phytomonas tumefaciens | 4,400 | 8,000 |
| Proteus vulgaris | 3,000 | 6,600 |
| Pseudomonas aeruginosa | 5,500 | 10,500 |
| Pseudomonas fluorescens | 3,500 | 6,600 |
| Salmonella enteritidis | 4,000 | 7,600 |
| Salmonela paratyphi - Enteric fever | 3,200 | 6,100 |
| Salmonella typhosa - Typhoid fever | 2,150 | 4,100 |
| Salmonella typhimurium | 8,000 | 15,200 |
| Sarcina lutea | 19,700 | 26,400 |
| Serratia marcescens | 2,420 | 6,160 |
| Shigella dyseteriae - Dysentery | 2,200 | 4,200 |
| Shigella flexneri - Dysentery | 1,700 | 3,400 |
| Shigella paradysenteriae | 1,680 | 3,400 |
| Spirillum rubrum | 4,400 | 6,160 |
| Staphylococcus albus | 1,840 | 5,720 |
| Staphylococcus aerius | 2,600 | 6,600 |
| Staphylococcus hemolyticus | 2,160 | 5,500 |
| Staphylococcus lactis | 6,150 | 8,800 |
| Streptococcus viridans | 2,000 | 3,800 |
| Vibrio comma - Cholera | 3,375 | 6,500 |

*it is noted that American Ultraviolet Company (Lebanon, IN, USA) states that the energy dosage of UV radiation (UV Dose) shown above to kill 99% of the indicated microorganisms, is sufficient to achieve a 100% kill factor of the indicated microorganism.

Table 3 provides the approximate required intensities to kill or growth inhibit ("Kill Factor") either 90% or 99% of protozoa (American Water & Air® Inc., Hilton Head Island, S.C. 29926, USA):

| Protozoa | Energy Dosage of UV Radiation (UV Dose) in µWs/cm² Needed for Kill Factor | |
|---|---|---|
| | 90% (1 log Reduction) | 99%* (2 log Reduction) |
| Chlorella vulgaris (Algae) | 13,000 | 22,000 |
| Nematode Eggs | 45,000 | 92,000 |
| Paramecium | 11,000 | 20,000 |

*it is noted that American Ultraviolet Company (Lebanon, IN, USA) states that the energy dosage of UV radiation (UV Dose) shown above to kill 99% of the indicated protozoa, is sufficient to achieve a 100% kill factor of the indicated protozoa.

Table 4 provides the approximate required intensities to kill or growth inhibit ("Kill Factor") either 90% or 99% of viruses (American Water & Air® Inc., Hilton Head Island, S.C. 29926, USA):

| Virus | Energy Dosage of UV Radiation (UV Dose) in µWs/cm² Needed for Kill Factor | |
|---|---|---|
| | 90% (1 log Reduction) | 99%* (2 log Reduction) |
| Bacteriophage - E. Coli | 2,600 | 6,600 |
| Infectious Hepatitis | 5,800 | 8,000 |
| Influenza | 3,400 | 6,600 |
| Poliovirus - Poliomyelitis | 3,150 | 6,600 |
| Tobacco mosaic | 240,000 | 440,000 |

*it is noted that American Ultraviolet Company (Lebanon, IN, USA) states that the energy dosage of UV radiation (UV Dose) shown above to kill 99% of the indicated viruses, is sufficient to achieve a 100% kill factor of the indicated viruses.

Table 5 provides the approximate required intensities to kill or growth inhibit ("Kill Factor") either 90% or 99% of yeast (American Water & Air® Inc., Hilton Head Island, S.C. 29926, USA):

| Yeast | Energy Dosage of UV Radiation (UV Dose) in µWs/cm² Needed for Kill Factor | |
|---|---|---|
| | 90% (1 log Reduction) | 99% (2 log Reduction) |
| Brewers yeast | 3,300 | 6,600 |
| Common yeast cake | 6,000 | 13,200 |
| Saccharomyces carevisiae | 6,000 | 13,200 |
| Saccharomyces ellipsoideus | 6,000 | 13,200 |
| Saccharomyces spores | 8,000 | 17,600 |

*it is noted that American Ultraviolet Company (Lebanon, IN, USA) states that the energy dosage of UV radiation (UV Dose) shown above to kill 99% of the indicated yeast, is sufficient to achieve a 100% kill factor of the indicated yeast.

By way of example, using a germicidal UV lamp with 190 microwatts/cm² output at 254 nm, it would take approximately about 1 minute and 26 seconds to kill or growth inhibit ("Kill Factor") 100% of Saccharomyces sp. (which requires 17,600 microwatt/cm²) at a distance of 36" and 3 minutes 41 seconds at a distance of 60".

In some embodiments a UV lamp within a UV device has a polymer coating. The polymer coating will prevent small glass pieces from falling into a container in case of accidental shattering during use of a UV device in a method of the present invention.

B. Detector

The present invention describes a variety of UV devices. In some embodiments of the present invention, a UV device comprises a detector. In the drawings, detectors are shown by 11. The use of a detector ensures that in addition to the algorithm (taking into account vessel size and shape, lamp intensity, distance of lamp or lamps from surfaces to be sterilized) a required or predetermined UV light intensity is achieved. Further, a detector ensures that all areas known to specifically accumulate microorganisms also receive the required or predetermined dose of UV radiation.

The use of a detector solves a significant problem existing using the chemical and ozone disinfection methods. When those methods are used, there is no established protocol for verifying the level of sterilization achieved. In contrast thereto, methods of the present invention comprising the use of a detector offers a unique, quick, and reliable means of providing verifiable levels of the sterilization achieved. As described herein, once set at a predetermined UV dose, the detector will shut of the UV lamp when this predetermined amount of UV radiation has been attained.

In some embodiments of the present invention, a UV light source is connected to one or more UV detectors. In some embodiments of the present invention, a germicidal light source is connected to one or more UV detectors. As shown in the exemplary UV devices in FIGS. 6, 7, 14, and 15, one or more detectors may be mounted to a different position within the UV assembly or onto a removable bracket.

A variety of commercially available detectors can be used. UV-C detectors commercially available include, e.g., a PMA2122 germicidal UV detector (Solar Light Company, Inc., Glenside, Pa. 19038, USA). Detectors, such as the PMA2122 Germicidal UV detector, provide fast and accurate irradiance measurements of the effective germicidal radiation. A UV producing lamp is monitored to insure that the microorganisms, such as bacteria, are receiving a desired dose of germicidal UV radiation. Using a detector, the UV lamps can also be monitored to get maximum life out of the lamp before replacement. A germicidal UV detector can also be used to insure that the proper lamp has been installed after replacement.

In some embodiments of the present invention, a germicidal light source is connected electrically to one or more UV detectors. In some embodiments, a UV detector is connected by wire to a radiation meter, which in turn can communicate via the wire with a UV lamp and instruct it to turn off, e.g., when a desired radiation level has been attained.

In some embodiments of the present invention, a germicidal light source is connected to one or more UV detectors via a signal.

In some embodiments, a detector is placed at a location within a container where microorganisms, which negatively impact production and flavor of an alcoholic beverage, are known to accumulate.

In some embodiments of the present invention, the one or more UV detectors are placed in conjunction with a UV light source, preferably, a germicidal UV light source, so that the one or more detectors ensure that a desired UV intensity has been attained and/or maintained. In some embodiments, a detector is placed strategically in corners or on uneven surfaces of containers such as weld seams where microorganisms may accumulate.

In some embodiments, a detector is arranged so that it is both furthest away from the UV lamp and closest to the most uneven interior surface of a container (e.g., weld seam or a corner). The purpose of the detector is to ensure that the required or predetermined UV dose is attained at a given interior location of a container in order to achieve the desired log reduction of microorganisms. By placing a detector or more than one detector (i.e., at least two detectors) in one or more positions in the interior of the container, it will be ensured that the even surfaces and those closer to the UV lamp will receive more than sufficient UV radiation to achieve the desired log reduction of microorganisms and that the more problematic interior surfaces of a container (e.g., weld seams and corners) will receive the required or predetermined UV dose.

In some embodiments of the present invention, a UV light source communicates back and forth with a detector so that the UV light source is shut off when a desired specified germicidal level of UV radiation has been attained. As will be appreciated by one of skill in the art, a desired specified germicidal level is dependent on the log reduction or percentage reduction of microorganisms desired. If sterilization is required, a six log reduction in microorganisms may be specified. In the interest of saving time and electricity, however, a five log reduction or a four-log reduction may be desired. Once the desired UV intensity has been attained, the detector will cause the UV light source to shut off.

One of skill in the art using a detector in combination with a UV device to sterilize a container according to a method of the present invention would not need to know the diameter of the container as the detector would automatically detect the appropriate UV dose necessary to achieve a predetermined sterilization rate (log reduction value).

The use of a detector, however, is optional. Detectors are not required to practice methods of the present invention provided that the timing of the sterilization cycle has been calculated correctly. Detectors can be used as a redundant system if the shape of the container and/or lamp does allow the skilled artisan to apply a simple programmable calculation of the sterilization cycle duration.

C. Housing

In some embodiments of the present invention, a UV device comprises a housing. Various housings for UV lamps are shown in the exemplary UV devices in FIGS. 1-13, and 16 by 2. In some embodiments of the present invention, a germicidal UV light source is residing in a housing. In some embodiments of the present invention, a germicidal UV light source is positioned within a housing. The housing is designed to protect the UV light source from damage during transport or when it is retracted from a container according to a method of the present invention. The housing can be of a variety of materials. It can be made from a polymer (e.g., plastic) or metal depending on the desired weight.

Upon release of the germicidal UV light source from the housing, the germicidal UV light source may be stationary or mobile.

The housing maybe made of different materials. A preferred housing is made of DuPont Teflon® FEP (Fluorinated Ethylene Propylene).

D. Range-Finding Device

In some embodiments of the present invention where the UV lamp is mobile, a UV device comprises a range-finding device or guide, such as a laser range finder. A range-finding device may be placed or aligned at some point along the longitudinal axis of the UV device in order to prevent the UV lamp(s) or UV device from contacting either the top or bottom surface of the container (depending on the embodiment the device may be suspended from the top of the container or supported from below by a mount). If the embodiment uses lateral movement to position the UV lamp(s) closer to the internal surface the container, the rangefinder may be aligned in the same orientation ensuring that the UV lamp(s) is positioned at the desired distance depending on the internal diameter of the container. In some embodiments where the UV lamp is mobile, a range-finding device is used in conjunction with the system to guarantee that the UV lamp(s) is in correct distance from the interior surface of a container to be sterilized as well as preventing the UV lamp from impacting the interior surface of the container. Range-finding devices or guides are indicated by 20 in exemplary UV devices herein, e.g., in FIGS. 11 and 12.

E. Bracket

In some embodiments of the present invention, a UV device comprises a bracket. In some embodiments of the present invention, a housing is affixed to a bracket. The bracket essentially serves to place the UV lamp or the housing in which the UV lamp resides, on the outer perimeter of the opening of the container. In some embodiments, the bracket supports the housing in the desired position and allows the UV lamp to project and descend from the housing into the desired positions for the "sterilization cycle." In some embodiments, the bracket supports the housing centrally. In some embodiments, the bracket supports the housing asymmetrically. The bracket may be in the form of a base, tripod or stand if the device is to be supported from the bottom of the fermentation vessel. The arms of the bracket may be adjustable to accommodate containers of various diameters and dimensions. Exemplary bracket embodiments are depicted in the exemplary UV devices shown in FIGS. 1-5, and 10-12.

F. Optical Components

To increase the UV intensity over a reduced area, to focus the UV intensity, or to control the UV intensity, in some embodiments of the present invention, a UV device of the present invention comprises an optical component. Optical components include, but are not limited to, a reflector, a shutter, a lens, a splitter, a mirror, and the like. The optical component may be of any shape. In some embodiments of the present invention, a UV device comprises a reflector. A reflector can have a variety of configurations. In some embodiments, the reflector is a parabolic reflector. In some embodiments, the reflector is an elliptical reflector. In some embodiments, the reflector is a circular reflector. Exemplary embodiments comprising a reflector are depicted in the exemplary UV devices shown in FIGS. 12-14.

Reflectors are generally provided by the manufacturer of UV light sources. For example, reflectors of circular, elliptical and parabolic cross sections can be purchased from Hill Technical Sales Corp (Arlington Heights, Ill., USA). Exemplary reflectors are schematically shown in FIG. 18.

G. Additional Components of a UV Device

FIGS. 1-16 show exemplary embodiments in exemplary UV devices of the present invention. Those figures also show additional components of UV devices of the present invention, their positioning and how those components are connected to a container, a UV lamp, a UV detector, a frame, a bracket, a housing, and a range-finding device, which are described in detail above. Those additional components include a motorized unit (indicated by 1 in the figures), a cable or rigid rod (indicated by 7 in the figures), a base plate (indicated by 10 in the figures), a central sleeve (indicated by 12 in the figures), one or more connecting rods (indicated by 13 in the figures), a motorized sleeve (indicated by 14 in the figures), an adjustable bracket (indicated by 15 in the figures), a central post (indicated by 16 in the figures), parallelogramming arms (indicated by 17 in the figures), an arm (indicated by 18 in the figures; distinguished from "17"), a track on the arm (indicated by 19 in the figures); a second motor unit (indicated by 23 in the figures; different from the motorized unit "1", an "adjustable bracket" or "mounting frame" (indicated by 24 in the figures), track on central post (indicated by 25 in the figures), a lid (indicated by 29 in the figures), a hinged lid (indicated by 30 in the figures), a removable bracket (indicated by 31 in the figures), a reflector (indicated by 32 in the figures), nylon blocks (indicated by 33 in the figures), and a post or boss (indicated by 34 in the figures).

H. Positioning of UV Lamp

The UV lamp's positioning will be determined by e.g., the shape and volume of the vessel, steel type used, and the shape, size and power output of the lamp. Given the guidance provided herein, one of skill in the art will be able to properly position one or more UV lamps to achieve the desired killing or growth inhibition of one or more microorganisms using a method of the invention.

In some embodiments of the present invention, a UV lamp is suspended from a removable lid of a container of various dimension.

In other embodiments of the present invention, a UV lamp is suspended from a fixed or hinged lid of a container of various dimension.

In some embodiments of the present invention, the UV device is portable. A portable UV device can be transported between different vessels, vats and facilities.

I. Multiple UV Lamps

For use in the methods of the present invention, UV light sources, also referred herein as to UV lamps, can be configured in a variety of ways in a UV lamp assembly or UV device. The Configuration of one or more UV lamps within a UV device is referred to herein also as a UV lamp assembly. In some embodiments of the present invention more than one UV lamp is used for the sterilization of a container. Multiple UV lamps can be clustered together or spaced apart either symmetrically or asymmetrically in order to achieve the desired reduction in microorganisms in a timely and efficient manner.

For example, FIGS. 2 and 3 depict embodiments of the present invention where the UV assembly consists of a single UV lamp. FIG. 4 depicts an embodiment of the present invention showing a UV lamp assembly having four UV lamps. FIG. 5 depicts an embodiment of the present invention showing a UV lamp assembly having eight UV lamps arranged in an octagonal configuration. In addition, as depicted in FIG. 5, an additional UV lamp may be attached to a support plate. Those UV lamps are typically mounted to a frame 6, as shown, e.g., in FIGS. 4, 5, 14, and 15. Alternatively, those UV lamps are attached to or enclosed in a housing 2, as shown, e.g., in FIGS. 2, 3, 6-13, and 16. When more than one UV lamp is used in an UV assembly or in a method of the present invention, each UV lamp may be the same or different.

In some embodiments of the present invention a UV device comprises more than one UV lamp. In some embodiments, at least two UV lamps are clustered together. In some embodiments, at least three UV lamps are clustered together. In some embodiments, at least four UV lamps are clustered together. In some embodiments, four UV lamps are clustered together. In some embodiments, five UV lamps are clustered together. In some embodiments, six UV lamps are clustered together. In some embodiments, seven UV lamps are clustered together. In some embodiments, eight UV lamps are clustered together. The clustering of the lamps may be at perpendicular angles as shown in FIG. 4.

In some embodiments, more than one UV lamp is affixed to a bracket. In some embodiments, at least two UV lamps are affixed to a bracket. In some embodiments, at least three UV lamps are affixed to a bracket. In some embodiments, at least four UV lamps are affixed to a bracket. In some embodiments, four UV lamps are affixed to a bracket. In some embodiments, five UV lamps are affixed to a bracket. In some embodiments, six UV lamps are affixed to a bracket. In some embodiments, seven UV lamps are affixed to a bracket. In some embodiments, eight UV lamps are affixed to a bracket. The UV lamps may be affixed to a bracket as shown in FIGS. 1-5, and 10-15, which typically comprises mounting the UV lamp to a housing or frame and mounting the housing or frame to the bracket.

In some embodiments, more than one UV lamp is mounted on a frame. In some embodiments, at least two UV lamps are mounted on a frame. In some embodiments, at least three UV lamps are mounted on a frame. In some embodiments, at least four UV lamps are mounted on a frame. Four UV lamps may be mounted to a frame as shown exemplary in FIGS. 4-9, 12, and 15. In some embodiments, at least five UV lamps are mounted on a frame. In some embodiments, at least six UV lamps are mounted on a frame. In some embodiments, at least seven UV lamps are mounted on a frame. In some embodiments, at least eight UV lamps are mounted on a frame. Eight UV lamps may be mounted to a frame as shown exemplary in FIGS. 5 and 13.

J. Scissor Boom

In some embodiments of the present invention, a UV device is a scissor boom.

A scissor boom comprises a first end and a second end. The first end is also referred to as inner end, and the second end is also referred to as outer end.

In some embodiments, the scissor boom comprises at least one scissor unit between its first end and second end. In some embodiments, the scissor boom comprises at least two scissor units between its first end and second end. In some embodiments, the scissor boom comprises at least three scissor units between its first end and second end. In some embodiments, the scissor boom comprises at least four scissor units between its first end and second end. In some embodiments, the scissor boom comprises at least five scissor units between its first end and second end. In some embodiments, the scissor boom comprises at least ten scissor units between its first end and second end. A scissor unit can be made from any material. A preferred scissor bracket is a metal bracket. In some embodiments, a metal bracket is an aluminum bracket. Aluminum brackets are particularly preferred based on low cost and low weight. Preferred are also carbon fiber brackets. The scissor units are connected to each other by pivots. The pivots allow the horizontal extension of the scissor boom units.

The dimensions of a scissor boom for use in the methods of the present invention are not limited. A scissor boom may have various dimensions and may extend for several feet. A non-limiting scissor boom constructed by the Applicant measures about 10" by 10" by 50" in its retracted position and can extend over 15 feet.

In some embodiments of the present invention, an actuator unit is mounted to the first end of the scissor boom. An exemplary, non-limiting, embodiment of a linear actuator 37 is shown in FIG. 19. An actuator of the present invention operates by conversion of a rotary motion into a linear motion. An actuator extends the scissor boom and the extent of the expansion is determined by a sensor.

In some embodiments, a UV lamp 5 is mounted to the second end of the scissor boom. In some embodiments of this UV device, the UV lamp 5 is housed in a housing (e.g., FIG. 19). In some embodiments, a UV lamp cluster 41 (i.e., more than one UV lamp) is mounted to the second end of the scissor boom. In some embodiments of the present invention, a UV lamp cluster comprises at least two germicidal UV light sources. In some embodiments of the present invention, a UV lamp cluster comprises at least three germicidal UV light sources. In some embodiments of the present invention, a UV lamp cluster comprises at least four germicidal UV light sources. In some embodiments of the present invention, a UV lamp cluster comprises at least five germicidal UV light sources. In some embodiments of the present invention, a UV lamp cluster comprises two germicidal UV light sources. In some embodiments of the present invention, a UV lamp cluster comprises three germicidal UV light sources. In some embodiments of the present invention, a UV lamp cluster comprises four germicidal UV light sources. In some embodiments of the present invention, a UV lamp cluster comprises five germicidal UV light sources.

In some embodiments of this UV device, the UV lamp cluster 41 is housed in a UV lamp cluster housing 36 (FIG. 19). In some embodiments, the first end of the scissor boom is attached to an additional bracket mounted to a container (e.g., an adjusting bracket 24 as shown in FIG. 10) so that the scissor boom can be moved up and down via sliding rails 39 located at the inner end of the scissor boom (FIG. 19).

A scissor boom of the present invention can move (a) horizontally from an interior position of a container (i.e., from its folded position, FIG. 19A) towards the inner wall of the container (i.e., into its extended position, FIG. 19B) via slide rail 40, (b) vertically along sliding rails 39 in an up and down movement, and (c) in a circular motion when the scissor boom is fixed at a desired vertical position in the container and in its extended position. In the embodiments where the UV lamp(s) are within a housing, upon reaching the desired position, the UV lamp(s) are released and the housing is removed.

1. Horizontal Movement

In some embodiments of the present invention, a scissor boom comprises a UV lamp and a means for horizontally moving the UV lamp from an inner position of a container to an outer position of the container. The same means for moving the UV lamp from the inner position of the container to the outer position of the container can be used to move the UV lamp from the outer position of the container to an inner position of the container.

Effectuating a horizontal movement of a scissor boom, i.e., extending a scissor boom from its folded position to its extended position can be done manually or via a motorized unit. Manual extension of a scissor boom to a desired position can be done when the distance between the UV lamp(s) and the inner wall of the container is constant, i.e., in a container with straight walls and where the interior diameter throughout the height of a container will be constant.

Some containers, such as wooden wine barrels, however, often do not have straight walls. In those containers, the interior diameter of a container varies. The diameter typically is smallest at the top and bottom of the container and the greatest at the middle of the container. For those containers a controllable motorized extension and retraction of the scissor boom is preferred.

Figure 19B:
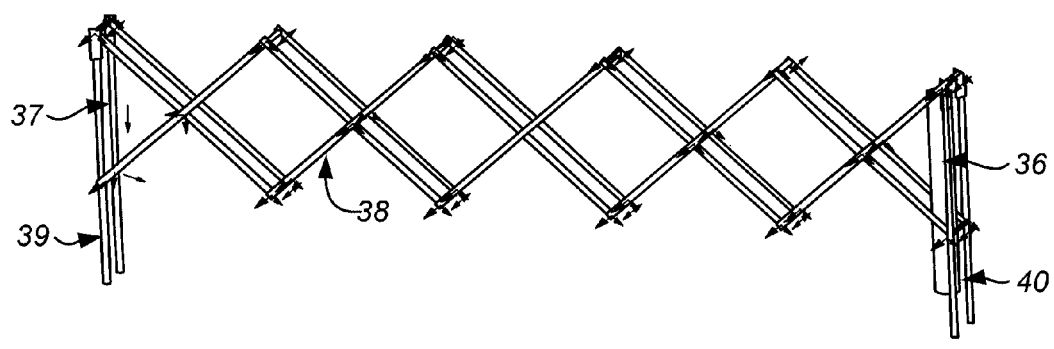

Thus, in some embodiments extending a scissor boom to a desired position is performed by a motorized unit, also referred to as a motor unit. In some embodiments of the present invention, a scissor boom comprises a motor unit for effectuating the horizontal movement of a UV lamp mounted to a second end of the scissor boom to an inner wall of a container. The motor unit then essentially expands the scissor units of the scissor boom so that the UV lamp(s) mounted at the opposite end (outer end) of the scissor boom than the motor unit can be positioned at a desired position within a container. Upon activation of the scissor mechanism, the one or more UV lamps attached to the outer end of the scissor boom move from its (their) folded position (FIG. 19A) towards an extended position (FIG. 19B). This movement is horizontally towards the inner wall of a container (and backwards to its folded position). In its extended position, the UV lamps of the scissor boom are close to the inner wall of the container so that when activated (switched on), the desired effect on the microorganisms present on the wall of the container will be achieved (as described herein).

In some embodiments, the motorized unit is attached to the first end of scissor boom. In some embodiments, a sensor is attached to the scissor boom. The sensor can be attached to the second end of the scissor boom, e.g., in close proximity to a UV lamp. In some embodiments, the sensor, such as a laser range finder described herein, is attached to sliding rail 40. The sensor measures the distance from the UV lamp(s) to the wall of the container. The sensor is connected to the motorized unit for extending and retracting the scissor boom. The sensor effectively guarantees that the UV lamp(s) are positioned in the same distance to the inner wall of the container. In case where the sensor senses that the UV lamp(s) is too far away from the inner wall of the container, it sends a signal to the motor unit, which then extends the scissor mechanism accordingly allowing the UV lamp(s) to be moved closer to the inner wall of the container until a desired position is achieved. Likewise, should the sensor sens that the UV lamp(s) are too close to the inner wall of the container, it sends a signal to the motor unit, which then retracts the scissor mechanism accordingly allowing the UV lamp(s) to move further away from the inner wall of the container until a desired position is achieved. Thus, the sensor is connected to the motor unit.

A preferred means for effectuating the horizontal movement of the scissor boom is an actuator.

2. Vertical Movement

In some embodiments of the present invention, a scissor boom comprises a UV lamp and a means for vertically moving the UV lamp from an upper position within a container to a lower position of the container. The same means for moving the UV lamp from the upper position within a container to the lower position of the container can be used to move the UV lamp from the lower position within the container to an upper position of the container.

In some embodiments of the present invention, a means for moving a UV lamp from an upper position within a container to a lower position within a container and/or from a lower position within a container to an upper position within a container is by using an actuator. Thus, in some embodiments, a scissor boom comprises an actuator. An exemplary scissor boom is shown in FIG. 19. A preferred means for effectuating the vertical movement of the scissor boom is an actuator.

An actuator is a mechanical device for moving a UV lamp to a desired position within a container. In some embodiments, the actuator is a linear actuator. An actuator of the present invention actuates up and down (or in a lateral direction) and moves a cross bar with it effectively extending and retracting a scissor mechanism (FIG. 19).

In some embodiments, the linear actuator is mounted to a bracket.

In some embodiments, the linear actuator 37 is a DC linear actuator. In some embodiments, the linear actuator 37 is an AC linear actuator.

The force of the actuator can vary significantly, however, will be sufficient to move a UV lamp to a desired position within a container. In some embodiments, the force of an actuator is at least 100 lbs. In some embodiments, the force of an actuator is at least 200 lbs. In some embodiments, the force of an actuator is at least 300 lbs. In some embodiments, the force of an actuator is at least 500 lbs. In some embodiments, the force of an actuator is at least 750 lbs. In some embodiments, the force of an actuator is at least 1,000 lbs. In some embodiments, the force of an actuator is at least 1,200 lbs.

3. Circular Movement

In some embodiments of the present invention, a scissor boom comprises a UV lamp and a means for circular moving one or more UV lamp(s) from one position within a container to another position of the container. A motorized unit (motor unit) can be used to effectuate the circular movement of the one or more UV lamp(s). Preferably, a sensor is attached to the second end of the scissor boom and sends signals to a second motorized unit (motor unit) for extending and/or retracting the scissor mechanisms to adjust for the respective distance between the UV lamp(s) and the inner wall of the container.

A scissor boom can be mounted at its first end to an inner wall of a container or to a (removable) bracket as shown e.g., in FIG. 10. When mounted to an inner wall of a container at a first position or a bracket, the circular motion of the scissor boom is somewhat limited. The UV lamp(s) will, for example, not cover, and thus, not efficiently sterilize, the wall part of the inner container to which the scissor boom is mounted, i.e., the first position. Microorganisms present at around the first position may not be growth inhibited to the extent desired. This limitation can easily be overcome by mounting the scissor boom to the opposite position of its first mounting position, i.e., into a second position, and repeat the UV sterilization process.

To overcome the need for repositioning the scissor boom and to permit a complete circular rotation, in some embodiments of the present invention, a scissor boom is mounted to a central post, which can be positioned in the center of a container. In this embodiment, the circular motion of the scissor boom is such that it allows to cover 360° of the container, i.e., the complete inner walls of the container. The central post may reach to the bottom of the container and/or may be connected to a lid of the container or, alternatively to a bracket resting on top of the container for stabilization and desired positioning.

In some embodiments of the present invention, the circular movement of a scissor boom (when extended) is done manually by pivoting the UV device. The UV device may be set in a position upon installation in the center of a container that will allow the scissor boom to extend from the center of the container to the outer region of the container. Alternatively, the UV device may be set in a position upon installation at a wall of a container that will allow the scissor boom to extend from the wall of the container to the outer region of the container.

The speed of the circular motion of the scissor boom is adjusted to obtain a desired effect, i.e., the growth inhibition of microorganisms present on the inner wall of the container.

K. UV Lamp Cluster Assembly

In some embodiments of the present invention, a UV lamp is configured into a bulb cluster assembly. Increasing the number of UV lamps increases the intensity of UV light emitted throughout the tank or container. For packaging purposes, multiple short UV lamps are preferable to fewer long UV lamps. The increased UV intensity decreases the time necessary for sterilization or sanitization.

An exemplary bulb cluster assembly of a UV device is shown in FIG. 20. While FIG. 20 shows that the UV lamps are not in a housing, in some embodiments, UV lamps may be in a protective housing. UV lamps assembled into a bulb cluster assembly are spring loaded. As they emerge from the housing, they spring out to a relatively optimal angle of 15 degrees. Other preferred angles are 10 degrees, 11, degrees, 12, degrees, 13 degrees, 14 degrees, 16 degrees, 17 degrees 18 degrees, 19 degrees, and 20 degrees. These angles are preferred as they allow for good UV coverage on both horizontal and vertical surfaces of a container.

L. UV Lamp Cluster Assembly Combined with Scissor Boom

In some embodiments, a UV device of the present invention comprises a UV lamp cluster and a scissor boom. In some embodiments, a UV lamp cluster comprise three UV lamps. In some embodiments, a UV lamp cluster comprise four UV lamps. In some embodiments, a UV lamp cluster comprise five UV lamps. The function of the scissor boom mechanism is to move the UV lamps horizontally across the top of a container and position the UV lamps to the central axis of the container. A linear actuator (37 in FIG. 19) pushes the scissor mechanism up and down a slide rail (39 in FIG. 19) allowing the length of the scissor to be varied according to the diameter of the container. Slide rails (40 in FIG. 19) on the second side of the scissor boom allow the system to expand and contract in length. Once in place, the UV lamp cluster is dropped from its housing, if present (36, in FIG. 19), and lowered down the central axis of the container.

Figure 20A:
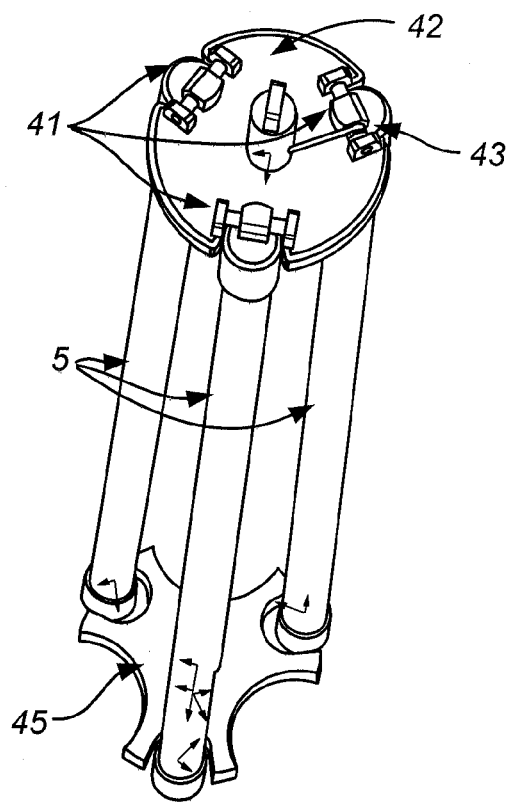
FIG. 20 depicts an embodiment of a UV device of the present invention referred to as bulb cluster assembly. A. closed configuration; B, open configuration. In this embodiment, the bulb cluster assembly is shown without a protective housing. In other embodiments, the UV lamps 5 are in a protective housing when not in use. Three UV lamps 5 are attached via pins 41 to an upper plate 42. When dropped out of a protective housing (not shown), a spring 43 on each UV lamp (only shown for one UV lamp in Figure) forces the UV lamps out to a 15 degree angle. A central bar 44 attaches to a lower plate 45 to the upper plate 42. As the cluster is retracted back into the protective cover, the UV lamps are forced back into a vertical position and are held in place by the lower plate 45.
Figure 20B:
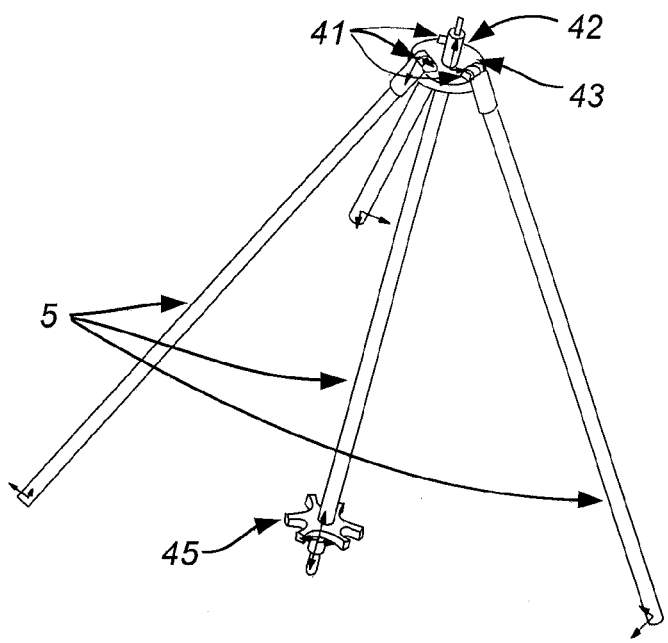

The UV lamp cluster may be housed in a protective housing 36 (FIG. 19) and can be attached to a winch at the second end of a scissor mechanism. Once the linear actuator extends the scissor boom to the central position in the tank, the winch drops the UV lamp cluster from the protective cover. As this occurs, the UV lamps will spring out into a tripod configuration in case three UV lamps were clustered (FIG. 20B). An algorithm based on the diameter and depth of the tank will determine the speed at which the winch lowers and raises the tripod configuration. These distances may be determined either by ultrasonic or laser range finders. As the winch retracts the lamp back into the protective housing, the lamps are forced back into a vertical position and secured in that position by the lower plate (FIG. 20A). The scissor arm is then retracted and the system can be removed from the tank.

The entire UV device unit can be mounted to the port of a tank via either a molding attached to the slide rails. This molding or bracket can be made from a variety of materials, including various polymers, aluminum or other metals or carbon fiber. Preferably, it will be made for the lightest and most cost effective material. The standard access port on most modern tanks is offset to one side of the tank and is 18" in diameter.

III. Containers

In some embodiments, a UV device, preferably a UV light source, more preferably a germicidal UV light source, is introduced into a container. In some embodiments, a container is exposed to UV radiation. A container accepts a UV light source for the purpose of sterilization of the interior of the container, including any and all objects, fluids, materials, and surfaces contained within the interior of the container. In some embodiments, the objects, fluids, materials, and surfaces within the interior of the container are contained within the container temporarily. In other embodiments, they are contained within the container permanently.

The present invention provides a variety of containers. Containers, include, but are not limited to a vat, a silo, a tub, a basket, a case, a box, a barrel, a storage bin, a container for biological fluids, a beverage container, and an aquarium.

A container for biological fluid includes, but is not limited, to a container for blood, a container for blood products, a container for a fermentation product, a container for a cell culture product, or a container for a biotechnology product. In some embodiments, a fermentation product is an alcoholic beverage.

A beverage container includes, but is not limited, to a beverage container for water, milk, coffee, tea, juice, an alcoholic beverage, or a carbonated beverage. An alcoholic beverage includes, but is not limited to beer, wine, gin, vodka, or whisky.

Containers of various sizes, shapes, heights, and diameters can be used in the methods of the present invention as long as they have at least one opening through which a UV device or a UV lamp can be introduced.

Containers of various refractive indexes can be used in the methods of the present invention.

Containers of various reflective nature can be used in the methods of the present invention. As indicated in the following table, different materials reflect different percentages of UV light (254 nm). One of skill in the art will appreciate the contribution of the reflectance of a material will have for achieving a desired UV intensity useful for UV disinfection and sterilization (see Table 6).

TABLE 6

Reflective Factors On Various Surfaces At 254 Nm Wavelength. The values are obtained at normal incidence. The percentage reflectances increases rapidly at angles greater than 75%. (American Ultraviolet Company, Lebanon, IN 46052, USA)

| Material | % Reflectance |
| --- | --- |
| Aluminum, etched | 88 |
| Aluminum, foil | 73 |
| Aluminum, polished commercial | 73 |
| Chromium | 45 |
| Glass | 4 |
| Nickel | 38 |
| Silver | 22 |
| Stainless steel | 20-30 |
| Tri-plated steel | 28 |
| Water paints | 10-30 |
| White cotton | 30 |
| White oil paint | 5-10 |
| White paper | 25 |
| White porcelain | 5 |
| White wall plaster | 40-60 |

In some embodiments of the present invention, the interior surface of a container is UV reflective.

In some embodiments of the present invention, the interior surface of a container is stainless steel.

A. Fermentation Container

In some embodiments of the present invention, a container is a container used in zymurgy or the production of an alcoholic beverage. A UV device of the present invention may be used in any large scale commercial steel vessel involved in the fermentation and production of an alcoholic beverage.

A fermentation container may be of various size, shape, height, and can be used in a method of the present invention as long as it has at least one opening through which a UV device or UV lamp can be introduced.

A fermentation container may be made of a variety of materials, including stainless steel, wood, plastic, concrete, a polymer, or glass. A preferred fermentation container is made of wood.

IV. Systems

In another aspect of the present invention, systems comprising a UV device described herein, are provided. In some embodiments of the present invention, a system comprises a UV device. A UV device may include one or more components as described herein, e.g., a germicidal UV light source, a detector, a housing, a range-finding device, a bracket, an optical component, and/or a motorized unit. In some embodiments of the present invention, a system comprises a UV device and a container.

In some embodiments of the present invention, a system is for use in a method for ultraviolet (UV) sterilization of an interior surface of a container.

In some embodiments of the present invention, a system is for use in a method for inhibiting the growth of one or more species of microorganisms present in a container, preferably for inhibiting the growth of one or more species of microorganisms present on an interior surface of a container.

V. Methods

In another aspect of the present invention, methods of using a UV device described herein, are provided. In some embodiments, a method of using a UV device is a method for ultraviolet (UV) sterilization of an interior surface of a container. In some embodiments, the method for UV sterilization of an interior surface of a container comprises the steps of (a) providing a container having an opening, (b) movably inserting through the opening of the container a first germicidal UV light source and (c) activating the germicidal UV light.

In some embodiments, a method of using a UV device is a method for inhibiting the growth of one or more microorganisms present on an interior surface of a container. In some embodiments, the method for inhibiting the growth of one or more microorganisms present on an interior surface of a container comprises the steps of (a) providing a container having an opening, (b) movably inserting through the opening of the container a first germicidal UV light source and (c) activating the germicidal UV light.

The UV devices described herein and which are used in the methods described herein are not connected to or connected with or connectable to a container. As will be apparent by the examples and drawings provided herein, one of skill in the art will appreciate that a UV light source, such as a germicidal UV light source, is removably inserted into the interior of a containers.

A. Providing a Container

In some embodiments, the method for UV sterilization of an interior surface of a container comprises the step of providing a container having an opening. In some embodiments, the method for inhibiting the growth of one or more microorganisms present on an interior surface of a container comprises the step of providing a container having an opening. Containers useful for practicing methods of the present invention are described herein.

B. Inserting a UV Light Source into a Container

In some embodiments, the method for UV sterilization of an interior surface of a container comprises the step of inserting a germicidal UV light source through an opening of the container. In some embodiments, the method for inhibiting the growth of one or more microorganisms present on an interior surface of a container comprises the step of inserting a germicidal UV light source through an opening of the container. The opening of the container may be on top of the container as illustrated in FIGS. 1-3.

Alternatively, an opening of the container may also be at the bottom of a container or at a side of a container. One of skill in the art reading the instant specification will appreciate that a UV light source can be inserted into a container through an opening on the top, through an opening at the bottom, or through an opening at a side.

In some embodiments, once the UV light is inserted into a container, it remains in a stationary position for the time of the sterilization process. In some other embodiments, once the UV light is inserted into a container, it is mobile. In some embodiments, a UV lamp moves longitudinally within the container. In some embodiments, a UV lamp moves laterally. In some embodiments, a UV lamp rotates on its own axis or about an axis. In some embodiments, a combination of movements of some or all movements is used to achieve the desired result. The movement of the UV lamp is achieved through use of a motorized unit, a hydraulic system, or a combination thereof.

Mobility of the UV lamp depends on the size and shape of the container and on the size, shape, and intensity of the lamp. The use of a mobile UV lamp will depend on the desired sterilization rate. If, for example, a faster rate is desired, the UV lamp preferably is positioned closer to the inner surface of the container. Thus, in this embodiment, a means by which the UV lamp is positioned in closer proximity to the inner surface is necessary. Similarly, in some embodiments, the positioning of the UV lamp is altered to avoid an obstruction, such as an internally mounted thermometer or the like. As one of skill in the art will appreciate, the longitudinal movement of a UV lamp depends on the height of the vessel. Further, the lateral movement of a UV lamp depends on the diameter of the container. In embodiments where a rotating UV lamp is used, the rate of rotation will depend on the type of UV lamp used (continuous UVC vs. Pulsed UV) and the intensity of the UV lamp.

C. Activating a UV Light Source

In some embodiments, the method for UV sterilization of an interior surface of a container comprises the step of activating a germicidal UV light source. In some embodiments, the method for inhibiting the growth of one or more microorganisms present on an interior surface of a container comprises the step of activating a germicidal UV light source. Thereby a necessary or predetermined dose of radiation will be delivered. Activating of the UV light source initiates the process of sterilization, disinfection and growth inhibition of the one or more microorganisms by providing a UV dose for effective sterilization of microorganisms, disinfection of the interior surface of a container, and for the growth inhibition of the one or more microorganisms.

In some embodiments, the method for UV sterilization of an interior surface of a container comprises the step of manually activating a germicidal UV light source.

In some embodiments, activation of the UV light source occurs at a predetermined time.

In some embodiments, activation of the UV light source occurs for a predetermined time. Preferably the duration of the activation of the UV light source is provided for a time sufficient to cause an at least about 1 log reduction of microorganisms on the interior surface of a container, an at least about 2 log reduction of microorganisms on the interior surface of a container, an at least about 3 log reduction of microorganisms on the interior surface of a container, an at least about 4 log reduction of microorganisms on the interior surface of a container, an at least about 5 log reduction of microorganisms on the interior surface of a container, or an at least about 6 log reduction of microorganisms on the interior surface of a container.

By inserting the UV light source into the interior of a container and by activating the UV light source, the interior surface of the container is exposed to a UV light dose.

Once the desired UV intensity has been applied to the interior surface of a container, the UV light source may be deactivated. Deactivation is performed by a timer, which can be set to different times depending on the desired log reduction of the desired microorganisms (see calculations of killing rates in Example B). Deactivation can also be performed by a UV detector, which would automatically shut off the UV lamp(s) when the desired UV intensity has been attained. Again, the desired UV intensity will depend on the desired log reduction of the desired microorganisms. For example, using a lamp with an output of 190 microwatts/cm² at 254 nm (at a distance of 1 meter), placed within a fermentation vessel 60" from the interior surface, if a 2 log reduction of *Shigella dysentery* is desired, 4,200 microwatt seconds/cm² would be required. Once the UV detector has detected that 4,200 microwatt seconds/cm² have been attained it would automatically shut off the UV lamp. Thus, in some embodiments, the method for UV sterilization of an interior surface of a container comprises the step deactivating a germicidal UV light source. As described herein, deactivation may occur automatically by using a preset UV detector. Alternatively, deactivation is performed manually.

In some embodiments, the process of sterilizing the interior of a container comprises the step of subjecting the interior of the container to UV radiation.

While typically a single exposure of an interior surface of a container by a necessary or predetermined UV dose is sufficient to achieve a desired log reduction of microorganisms, in some embodiments, the interior surface of the container is exposed multiple times to UV radiation.

Short-wave UV light is harmful to humans. In addition to causing sunburn and (over time) skin cancer, UV light can produce extremely painful inflammation of the cornea of the eye, which may lead to temporary or permanent vision impairment. It can also damage the retina of the eye. For this reason, the light produced by a germicidal lamp must be carefully shielded against both direct viewing and reflections and dispersed light that might be viewed. Thus, in some embodiments of the present invention, the methods of sterilization a container and methods for inhibiting the growth of one or more microorganisms present on an interior surface of a container comprise the step of covering the container with a lid, top, or cover. The lid, top or cover essentially does not allow the UV light to penetrate and thus, protects humans from the harmful UV light.

D. Releasing the Germicidal UV Light Source from a Housing

In some embodiments, the method for UV sterilization of an interior surface of a container comprises the step of releasing the germicidal UV light source from the housing. In some embodiments, the method for inhibiting the growth of one or more microorganisms present on an interior surface of a container comprises the step of releasing the germicidal UV light source from the housing. Thereby a germicidal UV light source, e.g., a UV lamp, is released from a housing. The releasing of the germicidal UV light source from the housing is accomplished by a motorized unit. The motorized unit (exemplary shown in FIGS. 1-3) is connected to a rope or wire, which is connected to a UV lamp and thus, can move the UV lamp in an downward direction for use and moves the UV lamp in an upward direction after use.

In some embodiments, upon release from the housing, the germicidal UV light source moves longitudinally into the container to a predetermined position. An example of such a longitudinally movement is depicted in FIG. 3. In some embodiments, upon release from the housing, the germicidal UV light source moves laterally in the container to a predetermined position. An example of such a lateral movement is depicted in FIG. 7. In some embodiments, upon release from the housing, the germicidal UV light source rotates in the container. Examples of such a rotational movement are depicted in FIGS. 9-11.

E. Placing a Bracket Housing the Germicidal UV Light Source on the Upper Perimeter of a Container In some embodiments, the method for UV sterilization of an interior surface of a container comprises the step of placing a bracket housing the germicidal UV light source on the upper perimeter of a container. In some embodiments, the method for inhibiting the growth of one or more microorganisms present on an interior surface of a container comprises the step of placing a bracket housing the germicidal UV light source on the upper perimeter of a container. Thereby the UV device comprising the UV light source is firmly positioned on the upper perimeter of the container is restricted from moving downwards due to the brackets. An exemplary placing of a bracket housing the germicidal UV light source on the upper perimeter of a container is shown in FIGS. 3, 10, and 11. While the bracket is firmly placed on the upper perimeter of a container, as shown in FIGS. 3, 10, and 11 other parts of the UV device can be moved downwards into the container.

F. Movably Inserting Through the Opening of the Container a Second Germicidal UV Light Source In some embodiments, the method for UV sterilization of an interior surface of a container comprises the step of movably inserting through the opening of a container a second germicidal UV light source. In some embodiments, the method for inhibiting the growth of one or more microorganisms present on an interior surface of a container comprises the step of movably inserting through the opening of a container a second germicidal UV light source. The second germicidal UV light source can be inserted similarly as the first germicidal light source or different. Insertion of the second germicidal UV light source can be simultaneously with the first germicidal light source or subsequently. In some embodiments, the second germicidal light source differs from the first germicidal light source in dimension and/or intensity.

G. Inhibiting Growth of Microorganisms

In some embodiments of the present invention, a germicidal light source is used to inhibit the growth of a microorganism or inhibit the growth of one or more microorganisms. The terms "inhibiting the growth of microorganisms," "growth arresting microorganisms," "reducing microorganisms," "killing microorganisms," or grammatically equivalents are used interchangeably herein.

In some embodiments of the present invention, a microorganism is a yeast species. The following provides an non-exhaustive list of yeast species that are typically found in a fermentation container, and more specifically on an interior surface of a fermentation container. Yeast species that have been investigated for wine and beer production thus far include those from the *Candida, Kloeckera, Hanseniaspora, Zygosaccharomyces, Schizosaccharomyces, Torulaspora, Brettanomyces, Pichia, Hansenula, Metschnikowia, Torulespora, Debaryomyces, Saccharrmycodes* (species *ludwigii*), and *Williopsis* genera. Cultured yeast species include *Saccharomyces cerevisiae* and *Saccharomyces bayanus*. Non-Saccharomyces yeast in wine production is also being investigated. Thus, in some embodiments, it is particularly desirable to inhibit the growth of a yeast species using a method of the present invention. For example, 17,600 µWs/cm² is necessary for a 2 log killing of *Sacchahhmycodes* and 6,600 µWs/cm² for a 2 log killing of Brewer's yeast. UV intensities required for sterilization for unknown microorganism species can be determined by one of skill in the art using methods known in the art and described herein.

Some of the microorganisms found in a fermentation container, more specifically, on an interior surface of a fermentation container, are pathogenic. In some embodiments of the present invention, a microorganism is a pathogenic microorganism. Those microorganisms include, but are not limited to, *Escherichia coli, Corynebacterium diphtheria, Salmonella paratyphi* (causing enteric fever), *Salmonella typhosa* (causing typhoid fever), *Shigella dysenteriae* (causing dysentery), *Shigella flexerni* (causing dysentery), *Staphylococcus albus, Staphylococcus aureus, Streptococcus hemolyticus, Streptococcus lactis, Streptococcus viridians* and *Vibrio comma* (causing cholera). Thus, in some embodiments, it is particularly desirable to inhibit the growth of a pathogenic microorganism using a method of the present invention.

Other microorganisms found in a fermentation container, more specifically on an interior surface of a fermentation container, are detrimental in the production of a fermented beverage. Those microorganisms include, but are not limited to, *Brettanomyces (Dekkera)*, lactic acid bacteria, *Pediococcus, Lactobacillus*, and *Oenococcus. Brettanomyces* species include *B. abstinens, B. anomalus, B. bruxellensis, B. claussenii, B. custersianus, B. custersii, B. intermedius, B. lambicus*, and *B. naardensis*. The genus *Dekkera* (the perfect form of *Brettanomyces*, meaning it can sporulate), includes the species *D. bruxellensis* and *D. intermedius*. Thus, in some embodiments, it is particularly desirable to inhibit the growth of a microorganism, which is detrimental in the production of a fermented beverage, using a method of the present invention.

Other microorganisms found in a fermentation container, more specifically on an interior surface of a fermentation container, that are detrimental in the production of a fermented beverage are bacterial microorganisms. Bacteria genus include, but are not limited to, *Acetobacter, Lactobacillus, Pediococcus*, and *Leuconostoc. Acetobacter* species include, e.g., *A. aceti, A. hansennii, A. liquefaciens*, and *A. pasteurienus. Lactobacillus* species (ML bacteria, spoilage) include, e.g., *L. fructivorans* and others. *Pediococcus* species (ML bacteria, spoilage) include, e.g., *P. damnosus* and others. *Leuconostoc* species (ML bacteria) include, e.g., *L. o* and others. Thus, in some embodiments, it is particularly desirable to inhibit the growth of a bacterial microorganism using a method of the present invention.

1. Duration of Sterilization

The duration of sterilization, i.e., the time of activating a UV light source, determines the percentage of how many microorganisms are growth arrested or killed. As one of skill in the art will appreciate, the duration of a sterilization cycle is based on the power output of the UV lamp and the distance of the UV lamp from the walls and surfaces of the container to be sterilized.

In some embodiments, the duration of sterilization is performed for a time to ensure that at least 90% of the microorganisms present on the surface of a container are growth arrested or killed. One of skill in art will appreciate that a 90% growth arrest of microorganisms corresponds to a 1 log reduction.

In some embodiments, the duration of sterilization is performed for a time to ensure that at least 99% of the microorganisms present on the surface of a container are growth arrested or killed. One of skill in art will appreciate that a 99% growth arrest of microorganisms corresponds to a 2 log reduction.

In some embodiments, the duration of sterilization is performed for a time to ensure that at least 99.9% of the microorganisms present on the surface of a container are growth arrested or killed. One of skill in art will appreciate that a 99.9% growth arrest of microorganisms corresponds to a 3 log reduction.

In some embodiments, the duration of sterilization is performed for a time to ensure that at least 99.99% of the microorganisms present on the surface of a container are growth arrested or killed. One of skill in art will appreciate that a 99.99% growth arrest of microorganisms corresponds to a 4 log reduction.

In some embodiments, the duration of sterilization is performed for a time to ensure that at least 99.999% of the microorganisms present on the surface of a container are growth arrested or killed. One of skill in art will appreciate that a 99.999% growth arrest of microorganisms corresponds to a 5 log reduction.

In some embodiments, the duration of sterilization is performed for a time to ensure that at least 99.9999% of the microorganisms present on the surface of a container are growth arrested or killed. One of skill in art will appreciate that a 99.9999% growth arrest of microorganisms corresponds to a 6 log reduction.

2. Extinction Depths at 254 nm Wavelength

When practicing methods of the present invention, the extinction depths of the UV light source at 254 nm wavelength in various liquids needs to be taken into consideration, unless the surface of the container to be sterilized is completely dry. The application of UV light to sterilize a surface following a pressure wash would have to take into account the extinction depth of UV light at 254 nm in the remaining tap water. However, the depth of tap water the UV light must penetrate is minimal and would be equivalent to that of a film of water or at most interspersed water droplets. In some instances, the effect of depth of tap water on the duration of sterilization and kill rate will have to be tested using methods described herein and available in the art. This is due to the fact that following pressure washing of a container (e.g., a fermentation vessel), the remaining layer of water covering the container may not be homogeneous. Maximum depths of water drops can be used to calculate extra time needed for the sterilization cycle. Although the extinction coefficient could theoretically be used to calculate this, it would not take into account the reflection and scattering caused by uneven surfaces of the water film and water droplets, as such empirical data would be more useful for determining how to adjust sterilization timing. The following table provides guidance:

TABLE 7

Extinction Depths at 254 nm Wavelength (relationship to clear water) (American Ultraviolet Company, Lebanon, IN 46052, USA)

| Liquid | Extinction Depth |
| --- | --- |
| Apple juice | 1.0 |
| Beer | <1.3 |
| Liquid sugar | 1.0 |
| Milk - whole, raw | <0.1 |
| Vinegar | <5.0 |
| Water - concrete cistern | <75 |
| Water - distilled | 3,000 |
| Water - tap or mains | 125-180 |
| Wine | <2.5 |

H. Assessing Microbial Concentration

Microbial concentration on interior surfaces of containers may be assessed before and after performing a method of the present invention, such as the UV disinfection and UV sterilization methods described herein. A lower microbial concentration on interior surfaces of containers after a method of the present invention, e.g., performing a UV disinfection or UV sterilization method evidences the effectiveness of the method used. Methods for assessing microbial concentration are known in the art. Exemplary methods are described herein.

Preferred embodiments of this invention are described herein, including the best mode known to the inventor for carrying out the invention. Of course, variations on those preferred embodiments will become apparent to those of ordinary skill in the art upon reading the foregoing description. The inventor expects skilled artisans to employ such variations as appropriate, and the inventor intends for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or, otherwise clearly contradicted by context.

As can be appreciated from the disclosure above, the present invention has a wide variety of applications. While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention. The invention is further illustrated by the following examples, which are only illustrative and are not intended to limit the definition and scope of the invention in any way.

VI. Examples

The below examples are meant to illustrate specific embodiments of the methods and compositions described herein and should not be construed as limiting the scope of the invention in any way

Example 1

Assessing Microbial Concentration

The following is an exemplary method for assessing microbial concentration in a tank after UV disinfection according to a method described herein and after using the standard sodium hydroxide and citric acid procedure or hypochlorite and citric acid (Emmanuel et al., 2004, *Environmental International*, 30(7): 891-900).

i. Inoculation of a Container

Four tanks (wine fermentation vessels; stainless steel) are provided. Two tanks have a 36" radius and two tanks have a 60" radius and a height of 120". The tanks are pressure washed with water and inoculated with spoilage yeast, cultured yeast, and pathogenic microorganisms (see Table 8).

TABLE 8

Exemplary Inoculating Containers (Tanks) With Microorganism

| Spoilage Yeast | Cultured Yeast | Pathogenic Microorganisms |
|---|---|---|
| Brettanomyces abstinens | Saccharomyces cerevisiae | Salmonella spp |
| Brettanomyces anomalus | Saccharomyces bayanus | Clostridium botulinum |
| Brettanomyces bruxellensis | | Staphylococcus aureus |
| Brettanomyces claussenii | | Campylobacter jejuni |
| Brettanomyces custersianus | | Yersinia enterocolitica and Yersinia pseudotuberculosis |
| Brettanomyces custersii | | Listeria monocytogenes |
| Brettanomyces intermedius | | Vibrio cholerae O1 |
| Brettanomyces lambicus | | Vibrio cholerae non-O1 |

TABLE 8-continued

Exemplary Inoculating Containers (Tanks) With Microorganism

| Spoilage Yeast | Cultured Yeast | Pathogenic Microorganisms |
|---|---|---|
| Brettanomyces naardensis | | Vibrio parahaemolyticus and other vibrios |
| | | Vibrio vulnificus |
| | | Clostridium perfringens |
| | | Bacillus cereus |
| | | Aeromonas hydrophila and other spp |
| | | Plesiomonas shigelloides |
| | | Shigella spp |
| | | Miscellaneous enterics |
| | | Streptococcus |
| | | Escherichia coli enterotoxigenic (ETEC) |
| | | Escherichia coli enteropathogenic (EPEC) |
| | | Escherichia coli O157:H7 enterohemorrhagic (EHEC) |
| | | Escherichia coli enteroinvasive (EIEC) |

The tanks are inoculated on multiple surfaces, such as the corners, the weld seams, the bottom and sides of the tanks. After the inoculation and before the UV or chemical disinfection, samples are collected from several interior surfaces of the tanks (as described below). Those samples will be referred to as control samples or no treatment samples.

A UV light source, an American Air and Water UVC lamp 64" in length with an output of 190 microwatts/cm$^2$ at 254 nm (Model GML270) is inserted into a 36" radius tank (see, FIGS. 1-3) and activated for 1 minute and 26 seconds for each 64" interval of the tank. The UV-C lamp is moved down the 36" radius tank until the entire interior surface has been covered by the same intensity (dose) of UV-C light. After each interval of 1 minute and 26 seconds the UV lamp will be lowered by 64". In order to kill 100% of *Saccoromyces* sp. Yeast, 17,600 microwatt/cm$^2$ is needed (The timing of 1 minute and 26 seconds was based on achieving 17,600 microwatt/cm$^2$ at a distance of 36").

A UV light source, an American Air and water UVC lamp 64" in length with an output of 190 microwatts/cm$^2$ at 254 nm (Model GML270) is inserted into a 60" radius tank (see, FIGS. 1-3) and activated for 3 minute and 41 seconds for each 64" interval of the tank. The UV-C lamp is moved down the 60" radius tank until the entire interior surface has been covered by the same intensity (dose) of UV-C light. After each interval of 3 minute and 41 seconds the lamp will be lowered by 64" In order to kill 100% of *Saccoromyces* sp. Yeast, 17,600 microwatt/cm$^2$ is needed (The timing of 3 minute and 41 seconds was based on achieving 17,600 microwatt/cm$^2$ at a distance of 60").

The other 36" and 60" tanks, which have been comparably inoculated, are cleaned using the standard sodium hydroxide and citric acid solutions.

In a separate series of experiments, following inoculation, the tanks are sterilized/disinfected at different time intervals simulating alcoholic beverage production protocols (e.g., the time between tanks being emptied and then refilled).

ii. Collecting Samples from an Interior Surface of a Container

After completing the UV disinfection or the chemical disinfection as described above, the interior surfaces of the tanks are wiped using, e.g., Fellowes Surface Cleaning Wipes (STRATUS Inc., Amarillo, Tex.), which are premoisten antistatic wipes. Prior to the sampling, a sheet of original wipe cloth is cut to one forth size (48 cm$^2$) using sterilized scissors, placed into sterile whirl pack bags, and placed under a UV lamp for disinfection. Several areas of the tanks are wiped back and forth over the entire surface area of approximately 10 cm² using several vertical strokes, then folded with the fresh side of the wipe exposed, and several horizontal strokes were made over the same area with the other side of the wipe. After the sampling, the wipes are placed in 10 mL of phosphate buffer saline plus 0.01% Tween-80 (PBST) in 50-mL tubes. Types of sampling areas are recorded after the sampling.

iii. Microbial Assays

Collected wipe samples are assayed with culture methods to measure viable microorganisms. Selective agars, i.e. Tryptic(ase) Soy Agar (TSA) for mesophilic bacteria and thermophilic actinomycetes, Mannitol Salt Agar (MSA) for *Staphylococcus*, CHROMagar for methicillin resistant *Staphylococcus aureus* (MRSA) and Malt Extract Agar (MEA) for total fungi are used.

The log reduction of each inoculated microorganism species is recorded. Experiments are repeated to obtain statistically significant results.

iv. Pulsed UV Light

In a different series of experiments, the experiments described in i. to iii. of above, are repeated using a pulsed UV light. Xenon, SteriPulse-XL and Model RS-3000M will be used. As shown in FIG. 10, 11, or 16 one pulsed UV lamp will be mounted on laterally adjustable arms or mounts that allow the pulsed UV lamp to be brought within the optimal distance of 1.25" of the surface to be sterilized. The pulsed UV lamp uses an elliptical window and has a footprint of 16"×1". The pulsed UV lamp will be rotated at speed such that the footprint is exposed for a duration of 1 second on the surface being sterilized. For the tank with a 36" radius that means that the rate of rotation will be 0.277 rpm. After a 16" interval of the tank has been exposed to the pulsed UV, the device will be lowered by 16" and the rotation will be repeated. This will be repeated in 16" interval until the entire surface of the vessel has been exposed.

v. Closed Top Container

In a different series of experiments, the experiments described in i. to iv. of above, are repeated using a closed top fermentation vessel. Essentially, the only difference will be that instead of supporting the UV device by a bracket from the top of the fermentation vessel, the UV device will be mounted on a tripod and inserted through a hatch at the base of the fermentation vessel.

vi. Pressure Washing at Various Times

In a different series of experiments, the experiments described in i. to v. of above, are repeated by performing the pressure washing after various times following the inoculation. In this series of experiments it is also determined what, if any, effect the presence of water droplets will have on the log reduction. This is done by employing the UV device at various times following the pressure washing.

The first set of experiments involves inoculating the tanks and pressure washing them at different time intervals following inoculation, such as 24 hours, 48 hours, 72 hours and 144 hours. The pressure washing is then immediately followed by a UV sterilization cycle. This is done to determine whether the time bacteria and yeast are allowed to grow prior to pressure washing affects the final duration of the sterilization cycle.

Another set of experiments will not vary the time between inoculation and pressure washing, but rather the time between pressure washing and UV sterilization. The objective will be to determine the effects of varying amounts of water on the inner surface of the tank and its effect on the duration of the sterilization cycle and log reduction. In this set of experiments, the UV sterilization cycle can be applied at 0 minutes following the pressure washing, 15 minutes following the pressure washing and in continually increasing 15 minute intervals following the pressure washing until the tank is completely dry.

vii. Dry Interior Surface

In a different series of experiments, the experiments described in i. to vi. of above, are repeated by including the step of allowing the interior surface of the tanks to dry after performing the pressure washing.

Example 2

Calculating Killing of Microorganism

The following provides the steps to calculate the time needed to kill a desired microorganism using compositions and methods of the present invention. The required Energy Dosage of UV Radiation (UV Dose) in μWs/cm² needed for kill factor is provided herein in Tables 1-5. To determine the intensity of UV on a surface at various distances from a germicidal UV lamp one multiplies the radiant energy (shown in microwatts per square centimeter at one meter) by the intensity factor as shown in the Table 9 below.

TABLE 9

Intensity Factor (American Ultraviolet Company, Lebanon, IN 46052, USA

| | Distance from UV Lamp | | | | | | | | | |
|---|---|---|---|---|---|---|---|---|---|---|
| | 2" | 3" | 4" | 6" | 8" | 10" | 12" | 14" | 18" | 24" |
| Intensity Factor | 32.3 | 22.8 | 18.6 | 12.9 | 9.85 | 7.94 | 6.48 | 5.35 | 3.6 | 2.33 |

| | Distance from UV Lamp | | | | | | |
|---|---|---|---|---|---|---|---|
| | 36" | 39.37" (1 meter) | 48" | 60" | 80" | 100" | 120" |
| Intensity Factor | 1.22 | 1.0 | 0.681 | 0.452 | 0256 | 0.169 | 0.115 |

Using a UV lamp with an output of 190 microwatts/cm² at 254 nm (at a distance of 1 meter), placed within a fermentation vessel 36" from the interior surface, the following calculations are used for achieving 99% killing of *Saccharamyces carevisiae* (13,200 microwatt seconds/cm² required; see Table 5). Step 1: 13,200 microwatt seconds/cm²/190 microwatts/cm²=69.47 seconds. Step 2: The intensity factor at 36" is 1.22 (see Table 9), therefore 69.47 seconds/1.22=56.96 seconds.

Using a lamp with an output of 190 microwatts/cm² at 254 nm (at a distance of 1 meter), placed within a fermentation vessel 60" from the interior surface, the following calculations are used for achieving 99% killing of *Shigella dysentery* (4,200 microwatt seconds/cm² required; see Table 2): Step 1. 4,200 microwatt seconds/cm²/190 microwatts/cm²=22.10 seconds. Step 2: The intensity factor at 60" is 0.452 (see Table 9), therefore 22.10 seconds/0.452=48.90 seconds.

Using a lamp with an output of 190 microwatts/cm² at 254 nm (at a distance of 1 meter), placed within a fermentation vessel 60" from the interior surface, the following calculations are used for achieving 99% killing of *Sarcina lutea* (26,400 microwatt seconds/cm² required; see Table 2): Step 1. 26,400 microwatt seconds/cm²/190 microwatts/cm²=138.94 seconds. Step 2: The intensity factor at 60" is 0.452 (see Table 9), therefore 138.94 seconds/0.452=307.40 seconds.

Since *Sarcina lutea* is one of the most UV resistant bacteria (more resistant than known species of yeast), a fermentation vessel where the UV source was 60" away from the internal surface could be left on for about 307.40 seconds at each sterilization interval within the vessel to ensure all yeast (known) and pathogenic microorganisms are killed.

Example 3

Inhibiting the Growth of *Bacillus Subtilis*

To determine the effectiveness of a method of the present invention and efficacy of a UV device of the present invention for the sanitization of a stainless steel tank used in the wine making process, the killing/growth arrest of *Bacillus subtilis* (American Type Culture Collection, ATCC® Number 82™; designations: AMC [ATCC 8037, NRS 315]) was investigated. *Bacillus subtilus* forms spores, thereby making it a more UV resistant microorganism than microorganisms that do not form spores. In this experiment 30" SE UV-C lamps (Steril-Aire) were used. Three identical UV lamps were placed in a mount and put in a spiral configuration with each UV lamp set at a 15 degrees angle.

Two coupons (per time point) were spiked with a *Bacillus subtilus* suspension to give a final concentration of $9.6 \times 10^6$ CFU (colony forming units)/coupon for the first three time points. The fourth (25 minute) time point was inoculated with a suspension of $1.3 \times 10^7$ CFU/coupon (since it was tested on a different day) and allowed to air dry inside a biological safety cabinet. The coupons were allowed to dry and attached to the inside of stainless steel tank. Then the coupons were exposed to the UV light at a distance of 60" from the UV light source for four all four (4) time points: 30 seconds, 5 minutes, 15 minutes and 25 minutes. After each exposure time was performed, the coupons were swabbed in order to perform the recovery process. Two additional stainless steel coupons were spiked to be used as positive controls.

UV readings to measure the UV-C exposure at various time points were done using a General UV512C Digital UV-C Meter (radiometer). Table 10 below provides the actual UV readings recorded for each exposure time:

TABLE 10

UV Readings per Time Point and Interval.

| 30 Seconds Time Point | | 5 minutes Time Point | | 15 minutes Time Point | | 25 minutes Time Point | |
|---|---|---|---|---|---|---|---|
| seconds | uW | minutes | uW | minutes | uW | minutes | uW |
| 5 | 42 | 0.5 | 135 | 1 | 243 | 3 | 200 |
| 10 | 54 | 1 | 202 | 2 | 225 | 6 | 179 |

TABLE 10-continued

UV Readings per Time Point and Interval.

| 30 Seconds Time Point | | 5 minutes Time Point | | 15 minutes Time Point | | 25 minutes Time Point | |
|---|---|---|---|---|---|---|---|
| seconds | uW | minutes | uW | minutes | uW | minutes | uW |
| 15 | 69 | 1.5 | 206 | 3 | 212 | 9 | 174 |
| 20 | 87 | 2 | 204 | 4 | 198 | 12 | 167 |
| 25 | 109 | 2.5 | 202 | 5 | 186 | 15 | 162 |
| 30 | 135 | 3 | 198 | 6 | 177 | 18 | 159 |
|  |  | 3.5 | 195 | 7 | 176 | 21 | 162 |
|  |  | 4 | 192 | 8 | 181 | 24 | 169 |
|  |  | 4.5 | 190 | 9 | 175 |  |  |
|  |  | 5 | 184 | 10 | 172 |  |  |
|  |  |  |  | 11 | 171 |  |  |
|  |  |  |  | 12 | 171 |  |  |
|  |  |  |  | 13 | 171 |  |  |
|  |  |  |  | 14 | 170 |  |  |
|  |  |  |  | 15 | 168 |  |  |

The recovery of *Bacillus subtilis* from the coupons after 30 seconds exposure to the UV light was $5.3 \times 10^5$ CFU/ml. After 5 minutes exposure to the UV light, the recovery of *Bacillus subtilis* was reduced to $1.4 \times 10^3$ CFU/ml. After 15 minutes exposure to the UV light, the recovery of *Bacillus subtilis* was further reduced to $1.5 \times 10^1$ CFU/ml. Finally, after 25 minutes exposure to the UV light, no microorganisms were recovered. The recovery positive control had a count of $6.4 \times 10^5$ CFU/ml for the first three time points and $8.1 \times 10^5$ CFU/ml for the fourth time point.

Table 11 below summarizes the results of the above experiment and provides the log reduction results based on calculations from *Bacillus subtilis* recovery from test coupon vs. positive control.

TABLE 11

Inhibiting the growth of *Bacillus subtilis*

| Exposure Time | Concentration *Bacillus subtilis* Recovered (CFU/ml) | Log Reduction |
|---|---|---|
| 30 seconds | $5.3 \times 10^5$ | 0.1 |
| 5 minutes | $1.4 \times 10^3$ | 2.7 |
| 15 minutes | $1.5 \times 10^1$ | 4.6 |
| 25 minutes | 0 | 5.9 |

The results of this experiment demonstrated that the UV light source tested was effective in reducing the *Bacillus subtilis* microorganism population by about 3 logs at an exposure time of 5 minutes, by about 5 logs at an exposure time of 15 minutes and by about 6 logs at exposure time of 25 minutes.

One of skill in the art will appreciate that in view of the experiments described above, a lower UV dose will be required to kill or inhibit the growth of other microorganisms that do not produce spores. Thus, by having demonstrated that one of the most UV-resistant microorganisms can be efficiently killed or growth inhibited using a method of the present invention, one of skill in the art will appreciate that the methods of the present invention in combination with the UV devices of the present invention are useful to kill or growth inhibit other microorganisms that might be present in a fermentation container, more specifically on a surface of a fermentation container.

What is claimed is:

1. A method for ultraviolet (UV) sterilization of an interior surface of a container, the method comprising the steps of:

(a) movably and inwardly inserting through an opening of a container a portable UV device comprising a housing and a first germicidal UV light source;
(b) placing the portable UV device on or at an interior position within the container;
(c) releasing the first germicidal UV light source from the housing; and
(d) activating the first germicidal UV light source;
   wherein the first germicidal UV light source resides in the housing;
   wherein the first germicidal UV light source comprises a first UV lamp;
   and wherein the interior surface of the container is sterilized.

2. The method according to claim 1, wherein the germicidal UV light source is a pulsed germicidal UV light source.

3. The method according to claim 1, wherein the container is a container for fermenting an alcoholic beverage.

4. The method according to claim 3, wherein the alcoholic beverage is beer.

5. The method according to claim 3, wherein the alcoholic beverage is wine.

6. The method according to claim 1, wherein one or more species of microorganisms is present on the interior surface of the container and wherein the activation of the first germicidal UV light source results in inhibiting the growth of the one or more species of microorganisms.

7. The method according to claim 6, wherein the one or more species of microorganisms is selected from the group consisting of *Candida, Kloeckera, Hanseniaspora, Zygosaccharomyces, Schizosaccharomyces, Torulaspora, Brettanomyces, Saccharomycodes, Pichia, Williopsis, Peiococcus, Lactobacillus*, and *Oenococcus*.

8. The method according to claim 7, wherein the one or more species of microorganisms is *Lactobacillus*.

9. The method according to claim 6, wherein the growth of the one or more species of microorganisms is inhibited by at least 2 log.

10. The method according to claim 6, wherein the growth of the one or more species of microorganisms is inhibited by at least 3 log.

11. The method according to claim 6, wherein the growth of the one or more species of microorganisms is inhibited by at least 4 log.

12. The method according to claim 6, wherein the growth of the one or more species of microorganisms is inhibited by at least 5 log.

13. The method according to claim 6, wherein the growth of the one or more species of microorganisms is inhibited by at least 6 log.

14. The method according to claim 1, wherein the first germicidal UV light source is connected to a detector.

15. The method according to claim 14, wherein the detector measures a UV intensity level.

16. The method according to claim 14, wherein the detector shuts off the germicidal UV light source when a specified UV intensity level is attained.

17. The method according to claim 1, wherein the housing is attached to a central post and wherein the central post is attached to a plurality of horizontal stands.

18. The method according to claim 17, wherein the interior position within the container is a bottom of the container and further comprising the step of:
(e) placing the plurality of horizontal stands on the bottom of the container.

19. The method according to claim 1, wherein the interior position within the container is a bottom of the container and wherein step (b) comprises placing the portable UV device on the bottom of the container.

20. The method according to claim 1, further comprising the step of:
(c) movably and inwardly inserting through the opening of the container a second germicidal UV light source comprising a second UV lamp.

21. The method according to claim 20, wherein the first and second germicidal UV light sources are arranged in a cluster.

22. The method according to claim 21, wherein the cluster is selected from a cluster comprising at least two UV lamps, a cluster comprising at least three UV lamps, a cluster comprising at least four UV lamps, a cluster comprising at least five UV lamps, a cluster comprising at least six UV lamps, a cluster comprising at least seven UV lamps, and a cluster comprising at least eight UV lamps.

23. The method according to claim 20, wherein the first and second germicidal UV light source are spaced apart.

24. The method according to claim 20, wherein the first and second germicidal UV light sources are arranged adjustably so that they can be positioned at varying angles.

25. The method according to claim 24, wherein the angles are between 0 and 90 degrees.

26. The method according to claim 20, wherein the first and second germicidal UV light sources are arranged adjustably so that they can move in a circular motion.

27. The method according to claim 20, wherein the first and second UV light sources are attached to a plate.

28. The method according to claim 27, wherein springs attached to the plate force the first and second UV light sources from a closed configuration position into an open configuration position.

29. The method according to claim 28, wherein when moved into the open configuration position, the first and second germicidal UV light sources are arranged in an angle selected from the group consisting of 10 degrees, 11 degrees, 12 degrees, 13 degrees, 14 degrees, 15 degrees, 16 degrees, 17 degrees, 18 degrees, 19 degrees, and 20 degrees.

30. The method according to claim 1, wherein upon release from the housing, the first germicidal UV light source moves longitudinally to a predetermined position.

31. The method according to claim 1, wherein upon release from the housing, the first germicidal UV light source moves laterally in the container to a predetermined position.

32. The method according to claim 1, wherein upon release from the housing, the first germicidal UV light source rotates in the container.

33. The method according to claim 1, wherein the opening of the container is on top of the container.

34. The method according to claim 1, wherein the opening of the container is on a bottom of the container.

35. The method according to claim 1, wherein the opening of the container is on a side of the container.

36. The method according to claim 1, wherein the housing is attached to a central sleeve.

37. The method according to claim 36, wherein the central sleeve can be moved up and down within the container.

38. The method according to claim 1, wherein the housing is selected from the group consisting of a housing comprising a protective sleeve, a housing comprising a fan cooling system, a housing comprising a reflector, a housing attached to a bracket, a housing attached to a parallelogamming arm, a housing attached to a central sleeve, a housing attached to a scissor boom, a removable housing, and a housing which may fold open.

39. The method according to claim 1, wherein the interior position within the container is a bottom of the container; wherein the housing is attached to a central post; and wherein the central post is attached to a base plate, and further comprising the step of:
 (e) placing the has plate on the bottom of the container.

40. The method according to claim 1, further comprising the step of:
 (e) moving the first germicidal UV light source to a predetermined position within the container.

41. The method according to claim 40, wherein step (e) comprises moving the first germicidal UV light source longitudinally.

42. The method according to claim 40, wherein step (e) comprises moving the first germicidal UV light source laterally.

43. The method according to claim 40, wherein step (e) is performed by a motorized unit attached to the portable UV device.

44. The method according to claim 1, wherein the first UV lamp is selected from the group consisting of a hot cathode lamp, a slimline lamp, a high output lamp, and a cold cathode lamp.

45. The method according to claim 1, wherein the first UV lamp is selected from the group consisting of low pressure UV lamp, a medium pressure UV lamp and a high pressure UV lamp.

46. The method according to claim 1, wherein the portable UV device further comprises an optical component selected from the group consisting of a reflector, a shutter, a lens, a splitter, and a mirror.

47. The method according to claim 1, wherein the interior position within the container is a wall of the container and wherein step (b) comprises attaching the portable UV device to the wall of the container.

48. The method according to claim 47, wherein the portable UV device is attached to the wall of the container by an adjusting bracket allowing the attached UV device to be positioned within the container by an upwards movement and a downwards movement.

49. The method according to claim 47, wherein the attached UV device is a scissor boom comprising at least one scissor unit.

50. The method according to claim 49, wherein the scissor boom comprises a means for moving the first germicidal UV light source within the container, wherein the means for moving the first germicidal UV light source is selected from the group consisting of a means for horizontally moving the first germicidal UV light source from an inner position within the container to an outer position within the container, a means for horizontally moving the first germicidal UV light source from the inner position within the container to the outer position within the container, a means for vertically moving the first germicidal UV light source from an upper position within the container to a lower position within the container, a means for vertically moving the first germicidal UV light source from the lower position within the container to the upper position within the container, and a means for circular moving the first germicidal UV light source from a first position within the container to a second position within the container.

51. The method according to claim 1, wherein the container is a container for water, milk, coffee, tea, juice, an alcoholic beverage, or a carbonated beverage.

52. The method according to claim 1, wherein the container is selected from the group consisting of a vat, a silo, a tub, a basket, a case, a box, a barrel, a storage bin, a container for a biological fluid, a beverage container, and an aquarium.

53. The method according to claim 52, wherein the container for the biological fluid is selected from the group consisting of a container for blood, a container for a blood product, a container for a fermentation product, a container for a cell culture product, and a container for a biotechnology product.

54. The method according to claim 1, wherein the interior surface of the container comprises etched aluminum, foil aluminum, polished aluminum, chromium, glass, nickel, silver, stainless steel, tri-plated steel, water paint, white cotton, white oil paint, white paper, white porcelain or white wall plaster.

55. The method according to claim 1, wherein the container is made of stainless steel, wood, plastic, concrete, a polymer, or glass.

56. A method for ultraviolet (UV) sterilization of an interior surface of a container, the method comprising the steps of:
 (a) movably and inwardly inserting through an opening of a container a portable UV device comprising a motorized unit and a first germicidal UV light source;
 (b) placing the portable UV device on or at an interior position within the container; and
 (c) activating the first germicidal UV light source;
  wherein the first germicidal UV light source comprises a first UV lamp;
 wherein the motorized unit positions the first germicidal UV light source within the container;
  and wherein the interior surface of the container is sterilized.

57. A method for ultraviolet (UV) sterilization of an interior surface of a container, the method comprising the steps of:
 (a) movably and inwardly inserting through an opening of a container a portable UV device comprising a winch and a first germicidal UV light source;
 (b) placing the portable UV device on or at an interior position within the container; and
 (c) activating the first germicidal UV light source;
  wherein the first germicidal UV light source comprises a first UV lamp;
 wherein the winch positions the first germicidal UV light source within the container;
  and wherein the interior surface of the container is sterilized.

58. The method according to claim 56, wherein the germicidal UV light source is a pulsed germicidal UV light source.

59. The method according to claim 56, wherein the container is a container for fermenting a alcoholic beverage.

60. The method according to claim 56, wherein the container is a container for water, milk, coffee, tea, juice, an alcoholic beverage, or a carbonated beverage.

61. The method according to claim 60, wherein the alcoholic beverage is beer.

62. The method according to claim 60, wherein the alcoholic beverage is wine.

63. The method according to claim 56, wherein the container is selected from the group consisting of a vat, a silo, a tub, a basket, a case, a box, a barrel, a storage bin, a container for a biological fluid, a beverage container, and an aquarium.

64. The method according to claim 63, wherein the container for the biological fluid is selected from the group consisting of a container for blood, a container for a blood product, a container for a fermentation product, a container for a cell culture product, and a container for a biotechnology product.

65. The method according to claim 56, wherein the interior surface of the container comprises etched aluminum, foil aluminum, polished aluminum, chromium, glass, nickel, silver, stainless steel, tri-plated steel, water paint, white cotton, white oil paint, white paper, white porcelain or white wall plaster.

66. The method according to claim 56, wherein the container is made of stainless steel, wood, plastic, concrete, a polymer, or glass.

67. The method according to claim 56, wherein one or more species of microorganisms is present on the interior surface of the container and wherein the activation of the first germicidal UV light source results in inhibiting the growth of the one or more species of microorganisms.

68. The method according to claim 67, wherein the one or more species of microorganisms is selected from the group consisting of *Candida, Kloeckera, Hanseniaspora, Zygosaccharomyces, Schizosaccharomyces, Torulaspora, Brettanomyces, Saccharomycodes, Pichia, Williopsis, Pediococcus, Lactobacillus*, and *Oenococcus*.

69. The method according to claim 68, wherein the one or more species of microorganisms is *Lactobacillus*.

70. The method according to claim 67, wherein the growth of the one or more species of microorganisms is inhibited by at least 2 log.

71. The method according to claim 67, wherein the growth of the one or more species of microorganisms is inhibited by at least 3 log.

72. The method according to claim 67, wherein the growth of the one or more species of microorganisms is inhibited by at least 4 log.

73. The method according to claim 67, wherein the growth of the one or more species of microorganisms is inhibited by at least 5 log.

74. The method according to claim 67, wherein the growth of the one or more species of microorganisms is inhibited by at least 6 log.

75. The method according to claim 56, wherein the first germicidal UV light source is connected to a detector.

76. The method according to claim 75, wherein the detector measures a UV intensity level.

77. The method according to claim 75, wherein the detector shuts off the germicidal UV light source when a specified UV intensity level is attained.

78. The method according to claim 56, wherein the portable UV device further comprises a housing surrounding the first germicidal UV light source.

79. The method according to claim 78, wherein the housing is attached to a central sleeve.

80. The method according to claim 79, wherein the central sleeve can be moved up and down within the container.

81. The method according to claim 78, wherein the housing is selected from the group consisting of a housing comprising a protective sleeve, a housing comprising a fan cooling system, a housing comprising a reflector, a housing attached to a bracket, a housing attached to a parallelogramming arm, a housing attached to a central sleeve, a housing attached to a scissor boom, a removable housing, and a housing which may fold open.

82. The method according to claim 78, wherein the interior position within the container is a bottom of the container; wherein the housing is attached to a central post; and wherein the central post is attached to a base plate, and further comprising the step of:
(d) placing the base plate on the bottom of the container.

83. The method according to claim 56, wherein the interior position within the container is a bottom of the container and wherein step (b) comprises placing the portable UV device on the bottom of the container.

84. The method according to claim 56, further comprising the step of:
(d) movably and inwardly inserting through the opening of the container a second germicidal UV light source comprising a second UV lamp.

85. The method according to claim 84, wherein the first and second germicidal UV light sources are arranged in a cluster.

86. The method according to claim 85, wherein the cluster is selected from a cluster comprising at least two UV lamps, a cluster comprising at least three UV lamps, a cluster comprising at least four UV lamps, a cluster comprising at least five UV lamps, a cluster comprising at least six UV lamps, a cluster comprising at least seven UV lamps, and a cluster comprising at least eight UV lamps.

87. The method according to claim 84, wherein the first and second germicidal UV light source are spaced apart.

88. The method according to claim 84, wherein the first and second germicidal UV light sources are arranged adjustably so that they can be positioned at varying angles.

89. The method according to claim 88, wherein the angles are between 0 and 90 degrees.

90. The method according to claim 84, wherein the first and second germicidal UV light sources are arranged adjustably so that they can move in a circular motion.

91. The method according to claim 84, wherein the first and second UV light sources are attached to a plate.

92. The method according to claim 91, wherein springs attached to the plate force the first and second UV light sources from a closed configuration position into an open configuration position.

93. The method according to claim 92, wherein when moved into the open configuration position, the first and second germicidal UV light sources are arranged in an angle selected from the group consisting of 10 degrees, 11 degrees, 12 degrees, 13 degrees, 14 degrees, 15 degrees, 16 degrees, 17 degrees, 18 degrees, 19 degrees, and 20 degrees.

94. The method according to claim 56, wherein the first germicidal UV light source is moved longitudinally within the container to a predetermined position.

95. The method according to claim 56, wherein the first germicidal UV light source is moved laterally within the container to a predetermined position.

96. The method according to claim 56, wherein the first germicidal UV light source is rotated within the container.

97. The method according to claim 56, wherein the opening of the container is on top of the container.

98. The method according to claim 56, wherein the opening of the container is on a bottom of the container.

99. The method according to claim 56 wherein the opening of the container is on a side of the container.

100. The method according to claim 56, further comprising the step of:
(d) moving the first germicidal IV light source to a predetermined position within the container.

101. The method according to claim 56, wherein the first UV lamp is selected from the group consisting of a hot cathode lamp, a slimline lamp, a high output lamp, and a cold cathode lamp.

102. The method according to claim 56, wherein the first UV lump is selected from the group consisting of low pressure UV lamp a medium pressure UV lamp and a high pressure UV lamp.

103. The method according to claim 56, wherein the portable UV device further comprises an optical component selected from the group consisting of a reflector, a shutter, a lens, a splitter, and a mirror.

104. The method according to claim 56, wherein the interior position within the container is a wall of the container and wherein step (b) comprises attaching the portable UV device to the wall of the container.

105. The method according to claim 104, wherein the portable UV device is attached to the wall of the container by an adjusting bracket allowing the attached UV device to be positioned within the container by an upwards movement and a downwards movement.

106. The method according to claim 104, wherein the attached UV device is a scissor boom comprising at least one scissor unit.

107. The method according to claim 106, wherein the scissor boom comprises a means for moving the first germicidal UV light source within the container, wherein the means for moving the first germicidal UV light source is selected from the group consisting of a means for horizontally moving the first germicidal UV light source from an inner position within the container to an outer position within the container, a means for horizontally moving the first germicidal UV light source from the inner position within the container to the outer position within the container, a means for vertically moving the first germicidal UV light source from an upper position within the container to a lower position within the container, a means for vertically moving the first germicidal UV light source from the lower position within the container to the upper position within the container, and a means for circular moving the first germicidal UV light source from a first position within the container to a second position within the container.

* * * * *